US012759135B2

(12) United States Patent
Andon et al.

(10) Patent No.: US 12,759,135 B2
(45) Date of Patent: Oct. 13, 2026

(54) ENHANCED MOBILITY WEARABLE SYSTEM WITH SENSORY CUSHIONING SYSTEM

(71) Applicant: NIKE, Inc., Beaverton, OR (US)

(72) Inventors: Christopher Andon, Portland, OR (US); Summer L. Schneider, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 33 days.

(21) Appl. No.: 19/055,027

(22) Filed: Feb. 17, 2025

(65) Prior Publication Data

US 2025/0262756 A1 Aug. 21, 2025

Related U.S. Application Data

(60) Provisional application No. 63/554,537, filed on Feb. 16, 2024, provisional application No. 63/554,554, (Continued)

(51) Int. Cl.
*B25J 9/00* (2006.01)
*A61F 2/78* (2006.01)
(Continued)

(52) U.S. Cl.
CPC ........... *B25J 9/0006* (2013.01); *A61F 2/7843* (2013.01); *A61H 1/024* (2013.01); *A61H 1/0255* (2013.01);
(Continued)

(58) Field of Classification Search
CPC .............. A61F 2/7843; A61F 2002/501; A61F 2002/5061; A61F 2002/607; A61H 1/024; A61H 1/0255; A61H 1/0277; A61H 1/0281; A61H 3/00; A61H 2201/0103; A61H 2201/1215; A61H 2201/1246;
(Continued)

(56) References Cited

U.S. PATENT DOCUMENTS 9,808,390 B2 11/2017 Caires et al.
2005/0125078 A1* 6/2005 Br. Janusson ............ A61F 2/76 600/595
(Continued)

FOREIGN PATENT DOCUMENTS

CN 105796286 A 7/2016

OTHER PUBLICATIONS

Lee, Kang-Ho, et al. "A pneumatically controlled prosthetic socket for transfemoral amputees." Sensors 24.1 (2023): 133. (Year: 2023).
(Continued)

*Primary Examiner* — Dale Moyer
(74) *Attorney, Agent, or Firm* — Quinn IP Law

(57) ABSTRACT

A Smart Electro-Adaptive Reactive Airbag System ("SEARAS") provides for smart augmentation wearables and may incorporate any of a variety of wearable articles that provide for enhanced mobility, sensory, and/or stability augmentation for the wearer. The proprioceptive inputs and outputs may be tactile, neurological, or other stimuli perceptible, e.g., seen, felt, heard, smelt, tasted, or otherwise apprehendable or appreciable by the senses and/or mind of the wearer, including possible adjustments for the physicality of the wearer.

20 Claims, 15 Drawing Sheets

Related U.S. Application Data filed on Feb. 16, 2024, provisional application No. 63/554,528, filed on Feb. 16, 2024, provisional application No. 63/554,497, filed on Feb. 16, 2024, provisional application No. 63/554,547, filed on Feb. 16, 2024, provisional application No. 63/554,515, filed on Feb. 16, 2024, provisional application No. 63/554,564, filed on Feb. 16, 2024.

(51) Int. Cl.

| | |
|---|---|
| ***A61H 1/02*** | (2006.01) |
| ***A61H 3/00*** | (2006.01) |
| ***B25J 13/08*** | (2006.01) |
| ***B25J 19/00*** | (2006.01) |
| ***B25J 19/06*** | (2006.01) |
| *A61F 2/50* | (2006.01) |
| *A61F 2/60* | (2006.01) |

(52) U.S. Cl.

CPC ......... *A61H 1/0277* (2013.01); *A61H 1/0281* (2013.01); *A61H 3/00* (2013.01); *B25J 9/0009* (2013.01); *B25J 13/084* (2013.01); *B25J 13/085* (2013.01); *B25J 13/087* (2013.01); *B25J 13/088* (2013.01); *B25J 19/007* (2013.01); *B25J 19/06* (2013.01); *A61F 2002/501* (2013.01); *A61F 2002/5061* (2013.01); *A61F 2002/607* (2013.01); *A61H 2201/0103* (2013.01); *A61H 2201/1215* (2013.01); *A61H 2201/1246* (2013.01); *A61H 2201/1635* (2013.01); *A61H 2201/164* (2013.01); *A61H 2201/1645* (2013.01); *A61H 2201/165* (2013.01); *A61H 2201/5046* (2013.01); *A61H 2201/5064* (2013.01); *A61H 2201/5071* (2013.01)

(58) Field of Classification Search

CPC ...... A61H 2201/1635; A61H 2201/164; A61H 2201/1645; A61H 2201/165; A61H 2201/5046; A61H 2201/5064; A61H 2201/5071; B25J 9/006; B25J 9/009; B25J 13/084; B25J 13/085; B25J 13/087; B25J 13/088; B25J 19/007; B25J 19/06

See application file for complete search history.

(56) References Cited

U.S. PATENT DOCUMENTS

| | | | | |
|---|---|---|---|---|
| 2007/0038311 | A1 | 2/2007 | Kuiken et al. | |
| 2008/0071202 | A1 | 3/2008 | Nardi et al. | |
| 2014/0005577 | A1* | 1/2014 | Goffer .................. | A61H 1/0262 601/34 |
| 2014/0212243 | A1 | 7/2014 | Yagi et al. | |
| 2014/0260714 | A1 | 9/2014 | Vallery et al. | |
| 2014/0276264 | A1 | 9/2014 | Caires et al. | |
| 2015/0359644 | A1* | 12/2015 | Sanders .................... | A61F 2/80 623/34 |
| 2016/0030272 | A1 | 2/2016 | Angold et al. | |
| 2018/0092536 | A1* | 4/2018 | Sandler ................ | A61B 5/0024 |
| 2019/0029914 | A1* | 1/2019 | Polygerinos ......... | A61H 1/0237 |
| 2019/0343616 | A1 | 11/2019 | Stone | |
| 2019/0343707 | A1 | 11/2019 | Riener et al. | |
| 2021/0368925 | A1* | 12/2021 | Schneider .............. | A43B 13/20 |
| 2023/0099087 | A1 | 3/2023 | Kim et al. | |
| 2024/0325750 | A1 | 10/2024 | Hu et al. | |

OTHER PUBLICATIONS

Malhotra, "Soft Robotic Arms for Fall Mitigation: Design, Control, and Evaluation," 2022 (Year: 2022).

* cited by examiner

ENHANCED MOBILITY WEARABLE SYSTEM WITH SENSORY CUSHIONING SYSTEM

PRIORITY APPLICATIONS

This application claims the benefit of priority to U.S. Provisional Application Ser. No. 63/554,497, filed Feb. 16, 2024; U.S. Provisional Application Ser. No. 63/554,515, filed Feb. 16, 2024; U.S. Provisional Application Ser. No. 63/554,528, filed Feb. 16, 2024; U.S. Provisional Application Ser. No. 63/554,537, filed Feb. 16, 2024; U.S. Provisional Application Ser. No. 63/554,547, filed Feb. 16, 2024; U.S. Provisional Application Ser. No. 63/554,554, filed Feb. 16, 2024; and U.S. Provisional Application Ser. No. 63/554,564, filed Feb. 16, 2024, the contents of all which are incorporated herein by reference in their entireties.

BACKGROUND

Mobility enhancement devices, such as prosthetic limbs, exoskeletons, and the like, may improve, often to significant degrees, the ability of a wearer to engage in activities ranging from daily movement to athletic workouts. A prosthetic limb may replace at least some of the mobility lost as a result of a missing limb. An exoskeleton may significantly enhance already existing movement, including speed, strength, agility, and the like. Most or all such devices may be secured or otherwise attached to a limb or other body part of a wearer in order to provide the resultant mobility effect.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

While mobility-enhancing wearable devices can and do provide significant benefits to wearers, such benefits may be offset by potential issues. Such mobility-enhancing wearable devices may inhibit proprioception, the ability of the wearer to sense movement and action, or otherwise not provide as much proprioception as the wearer may ordinarily expect to experience in absence of the wearable device. The inclusion of inert mechanical components either entirely or almost entirely without connection to the wearer's nervous system may lead to disorientation by the wearer and provide a lack of environmental feedback to the wearer. For instance, the sense of the wearer that the wearable device has made contact with the ground may be highly attenuated if not eliminated altogether, resulting in reduced proprioception by the wearer and resultant instability or mental or physical disorientation.

Further, such mobility-enhancing wearable devices are known to cause discomfort to wearers at mechanical interfaces between the body of the wearer and the wearable device. Such wearable devices may rub or otherwise impart force on the skin or other parts of the body of the wearer which may result in irritation, fatigue, or even ongoing pain. While various cushioning systems may mitigate such conditions, such cushioning may be prone to degradation, may be of relatively minimal actual effectiveness, and may increase the loss of proprioception as the reduction in force on the wearer may also tend to reduce the mechanical inputs to the wearer that allow the wearer to sense the orientation of the wearable device and when the wearable device is contacting surfaces or other objects.

A system and mobility-enhancing wearable device and associated sensory cushion has been developed that combines sensors and haptic motors or haptic devices more generally integrated with an airbag. Such a Smart Electro-Adaptive Reactive Airbag System ("SEARAS") provides for smart augmentation wearables, as disclosed herein, and may incorporate any of a variety of wearable articles that provide for enhanced mobility, sensory, and/or stability augmentation for the wearer. The airbag may be included in the wearable device in a way that provides both sensing and feedback to increase wearer awareness of their surroundings and circumstances along with comfort that may exceed that of more conventional padding. Moreover, the airbag may be more resilient to forces imparted on it and less likely to experience degradation and/or permanent compression in comparison to most foams or other padding while also providing an improved platform for the inclusion of sensors and/or haptic devices in comparison with other padding.

Figure 1:
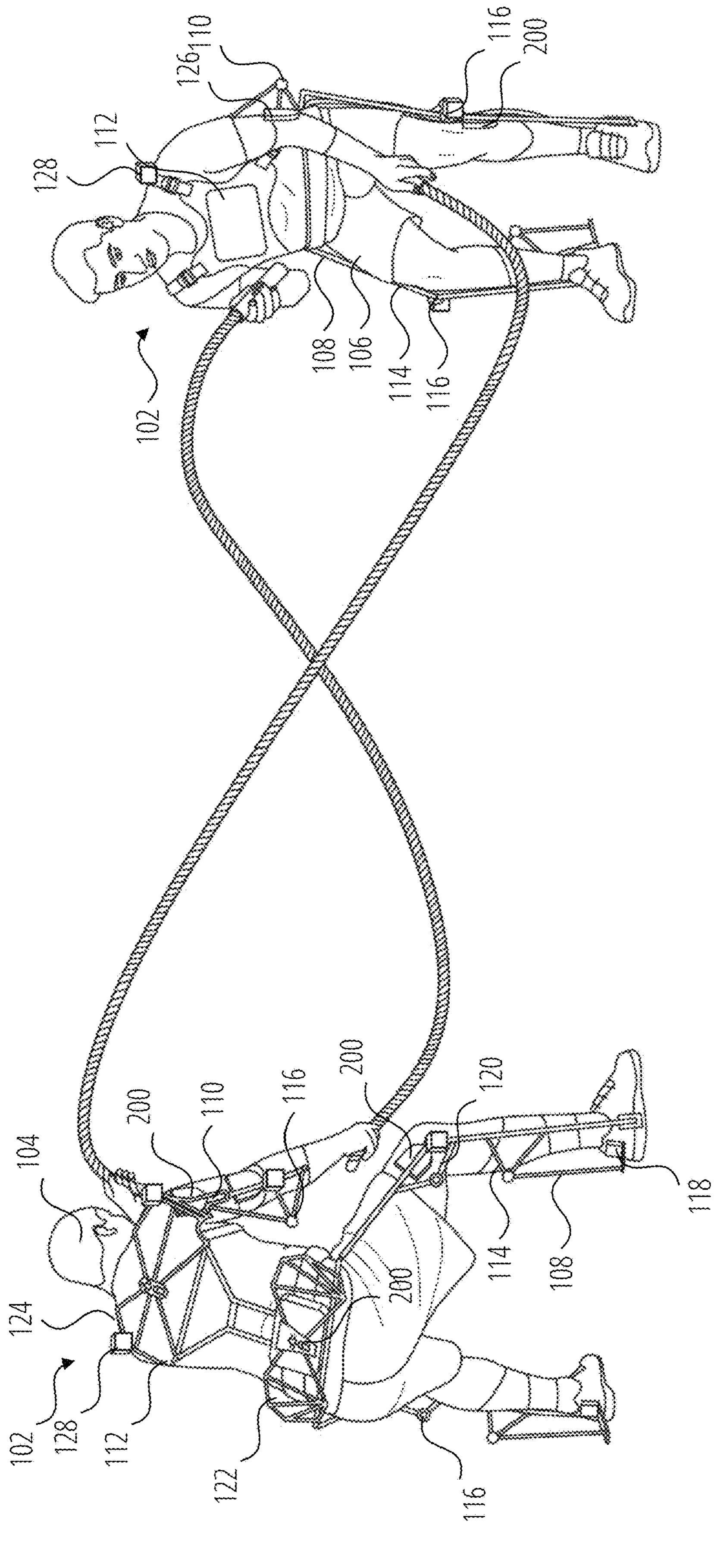
FIG. 1 is a depiction of enhanced wearable mobility articles being worn by wearers in the context of an athletic activity, in an example embodiment.

FIG. 1 is a depiction of enhanced wearable mobility articles 102 being worn by wearers 104, 106 in the context of an athletic activity, in an example embodiment. The enhanced wearable mobility articles 102 include various conventional exoskeleton components known in the art along with components that are disclosed in detail herein. Conventional exoskeleton components of the enhanced wearable mobility articles 102 in particular include a rigid frame 108 made from, e.g., metal, plastic or polymer, or other suitable material, configured to provide structural stability and support the weight of the wearers 104, 106 and/or an associated body part of the wearer as well as forces imparted by a motor, servo, or other mobility component of the enhanced wearable mobility article 102, as disclosed herein. The rigid frame 108 includes portions associated with various body parts of the wearers 104, 106, including arm structures 110, torso structures 112, and leg structures 114. The enhanced wearable mobility articles 102 further include joints 116 between the various structures 110, 112, 114 to permit flexibility of the enhanced wearable mobility articles 102 where desired. Additional components to provide conventional exoskeleton functionality, such control circuitry, a power source, and the like are included as components of the enhanced wearable mobility articles 102.

As disclosed in detail herein, the enhanced wearable mobility articles 102 further includes components not previously disclosed in the art. In particular, the enhanced wearable mobility articles 102 includes multiple sensory cushions (see FIG. 2, 200) positioned at various points of contact between the enhanced wearable mobility articles 102 and the body of the respective wearer 104, 106 (for the purposes of this disclosure, it is to be recognized and understood that the sensory cushions may, in various examples, be considered to be in contact with the body of the wearer even with materials, such as clothing, positioned between the skin of the wearer and the sensory cushion. In various examples, the sensory cushions may be positioned at or proximate some or all of foot portions 118, knee portions 120, a hip portion 122, shoulder portions 124, and elbow portions 126 of each of the enhanced wearable mobility article 102. It is noted that more than one sensory cushion may be positioned at each location; thus, for instance, multiple sensory cushions may be positioned around the hip portion 122, e.g., on each side and the rear of the hip portion 122. The locations described are for illustration and not limitation, and it is to be recognized and understood that a sensory cushion may be positioned at any location or position on the enhanced wearable mobility article 102 that comes into contact with the body of the wearer 104, 106 and at which the sensors and associated haptic devices may be desired to provide feedback to the wearer 104, 106.

The configuration of the enhanced wearable mobility article 102 thereby provides increased mobility to the wearer 104, 106 by providing increased stability and, in various examples, enhanced strength, dexterity, and other physiological attributes relevant to athletic activities. In the illustrated examples, the wearers 104, 106 are able to manipulate ropes in a coordinated way more strongly and easily than in absence of the enhanced wearable mobility articles 102 or with other exoskeletons known in the art. Moreover, as will be disclosed in detail herein, the wearers 104, 106 may experience greater comfort and responsiveness than with other exoskeletons. Motors 128 distributed proximate the joints 116 provide motive power to move portions of the rigid frame 108 with respect to one another about the joints 116. The motors 128 are operatively coupled to power supplies and control circuitry which operate with other componentry as disclosed herein to enable the enhanced wearable mobility articles 102 to enhance the strength, mobility, and stability of the wearers 104, 106.

While the discussion herein is primarily focused on the improvements in strength, mobility, and stability that the enhanced wearable mobility article 102 provides, it is to be recognized and understood that the enhanced wearable mobility article 102 may be utilized to adjust such physiological attributes in any way desired. Consequently, in various examples, the enhanced wearable mobility article 102 may oppose the motion of the wearer 104, 106, e.g., to strengthen the wearer 104, 106 as in resistance training or physical therapy. In various examples, the enhanced wearable mobility article 102 may add instability to the wearer 104, 106 in order to train the wearer 104, 106 for reaction time and to enhance the wearer's stability when not wearing the enhanced wearable mobility article 102. Moreover, the enhanced wearable mobility article 102 may be utilized to equalize or otherwise make more similar the athletic abilities between the wearers 104, 106. In an illustrative example, the enhanced wearable mobility article 102 of the wearer 104 may enhance the athletic abilities of the wearer 104 while the enhanced wearable mobility article 102 of the wearer 106 may inhibit the athletic abilities of the wearer 106 so as to make the wearers 104, 106 more equal in their abilities in the event of a disparity between them.

The enhanced wearable mobility article 102 may further provide a safety function for a wearer of the enhanced wearable mobility article 102. In various examples, in addition to providing enhanced stability and strength, the enhanced wearable mobility article 102 may further provide padding, including dynamic padding, for the wearer, e.g., in the event of a fall. In such examples, the enhanced wearable mobility article 102 may both provide kinetic support in the event of a fall, e.g., by providing rigidity or flexibility as desired to support the wearer and reduce the likelihood of injury, to providing variable pressure in airbags, e.g., airbag 402 as disclosed herein. Mechanisms for doing so are disclosed in U.S. Pat. No. 9,908,027, ARTICLE OF APPAREL WITH DYNAMIC PADDING SYSTEM, Beers, issued Mar. 6, 2018, which is incorporated by reference herein in its entirety.

The enhanced wearable mobility article 102 may incorporate any suitable technology to provide rigid stability along with control of the operation of the rigid frame 108, e.g., through motorized or other suitable means. In various examples, the enhanced wearable mobility article 102 may be implemented using mechanisms disclosed in U.S. Patent Application Publication No. 2022/0338562, ADAPTIVE APPAREL WITH SUPPORT CONTROL SYSTEM, Hopkins, filed Apr. 21, 2022; U.S. Patent Application Publication No. 2022/0338558, DIGITAL CONTROL SYSTEMS AND METHODS FOR ADAPTIVE APPAREL, Hopkins, filed Apr. 21, 2022; U.S. Patent Application Publication No. 2022/0338559, MECHANICAL CONTROL SYSTEMS AND METHODS FOR ADAPTIVE APPAREL, Hopkins, filed Apr. 21, 2022; U.S. Patent Application Publication No. 2022/0209689, ELECTROADHESIVES SYSTEM ISOLATION IN APPAREL, Walker, filed Nov. 29, 2022; U.S. Patent Application Publication No. 2023/0124653, SOLE STRCUTURE FOR ARTICLE OF FOOTWEAR AND ARTICLE OF FOOTWEAR, Farina, published on Apr. 20, 2023, all of which are incorporated by reference herein in their entirety.

Moreover, the rigid frame 108 itself may be formed from any suitable mechanism, including 3D printing techniques disclosed in U.S. patent application Ser. No. 19/008,289, SUPPORT GARMENT, and U.S. Ser. No. 19/008,592, SUPPORT GARMENT, and U.S. Ser. No. 19/008,594, SUPPORT GARMENT, all of which are incorporated by reference herein in their entirety. In various examples, the rigid frame 108 may incorporate various zonal properties to provide for relatively more rigid or flexible regions of the rigid frame 108. Consequently, while the rigid frame 108 may generally be understood to be rigid in general and supportive of the weight of the wearer, the rigid frame 108 may incorporate different zones of rigidity that work in conjunction with the joints 116 to provide mobility and support for the wearer 104 while maintaining comfort.

Figure 2:
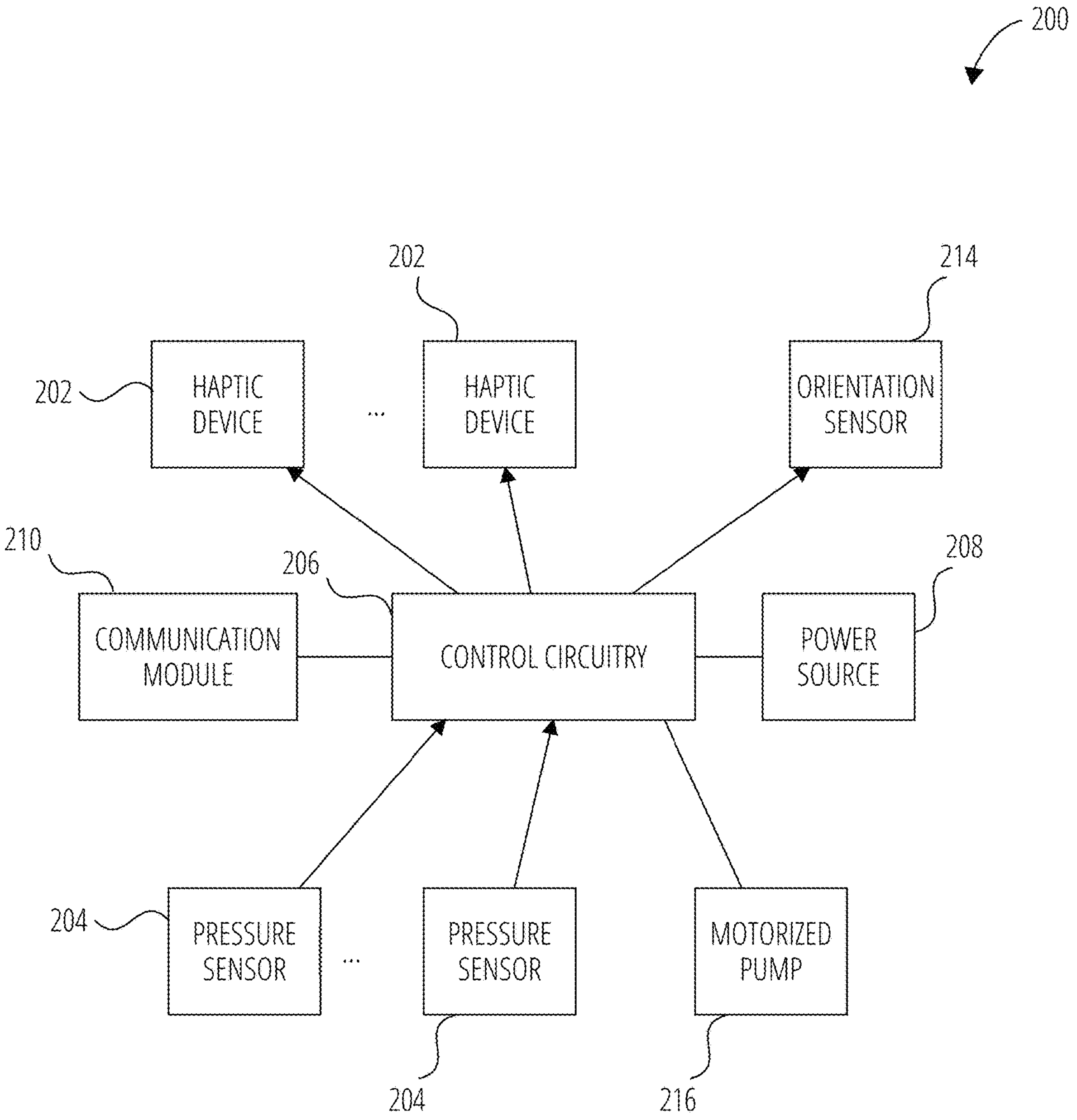
FIG. 2 is a block diagram of the electronic components of a sensory cushioning system configured to receive proprioceptive inputs and generate corresponding proprioceptive outputs, in an example embodiment.

FIG. 2 is a block diagram of the electronic components of a sensory cushioning system 200 configured to receive proprioceptive inputs and generate corresponding proprioceptive outputs, in an example embodiment. The proprioceptive inputs and outputs may be tactile, neurological, or other stimuli perceptible, e.g., seen, felt, heard, smelt, tasted, or otherwise apprehendable or appreciable by the senses and/or mind of the wearer, including possible adjustments for the physicality of the wearer. The sensory cushioning system 200 generally includes multiple haptic devices 202 and multiple pressure sensors 204 all operatively coupled to control circuitry 206 and to a power source 208. The sensory cushioning system 200 further optionally includes a communication module 210 configured to engage in electronic communications, e.g., with other sensory cushioning systems 200 that may be incorporated in the enhanced wearable mobility article 102 and/or another mobility-enhancing wearable article, as will be disclosed in detail herein, and/or with a remote computing system.

The control circuitry 206 may be or may include a controller or processor and any other electronic circuitry that may be useful in the context of the sensory cushioning system 200, including but not limited to electronic memory and/or electronic storage, etc. While the haptic devices 202 and the pressure sensors 204 may be local to the sensory cushioning system 200, some or all of the components of the control circuitry 206 may be remote to the sensory cushioning system 200 and may be accessed or be accessible by wired or wireless communications via the communication module 210.

The pressure sensors 204 are configured to sense the presence of force as exerted as pressure on the pressure sensors 204, e.g., by an external object. The external object may be any object that may induce a force detectable by the pressure sensor 204 when coming into contact with or in proximity of the pressure sensors 204 specifically and the sensory cushioning system 200 generally. While the pressure sensors 204 are described herein, it is to be recognized and understood the references to the pressure sensors 204 may also refer to force sensors or any other pressure or force sensing solution, e.g., as disclosed in U.S. Pat. No. 10,914,645, SYSTEM AND METHOD FOR ANALYZING ATHLETIC ACTIVITY, Rice, issued Feb. 9, 2021, U.S. patent application Ser. No. 18/660,671, FOOTWEAR LINER WITH ELECTRONICS TAB, Cobbett, filed May 10, 2024, and U.S. patent application Ser. No. 18/660,684, ARTICLE OF FOOTWEAR WITH LINER HAVING EXTERNAL GROUND PLANE, Cobbett, filed May 10, 2024, which are incorporated by reference in their entirety. Such external objects include but are not limited to a body part of a wearer or user of an object which includes the sensory cushioning system 200, an item on which the sensory cushioning system 200 has been included, or a medium into which the sensory cushioning system 200 may come into contact, such as a floor, the ground, a tabletop, a wall, etc. Objects that include the sensory cushioning system 200, objects which may engage with the system, and/or the circumstances in which the sensory cushioning system 200 may be utilized will be discussed in detail herein.

The pressure sensors 204 may be the same or different across the sensory cushioning system 200. Thus, for instance, one or more pressure sensors 204 be a first type of pressure sensor or a pressure sensor in a first configuration, e.

g., an airbag pressure sensor, while one or more of the pressure sensors 204 may be a second type of pressor sensor, e.g., a surface contact pressure sensor. Such different pressure sensors may be positioned in any physical configuration and be included in any suitable number or quantity to produce the desired sensitivity in the desired location of an object or objects with which the sensory cushioning system 200 is associated. The pressure sensors may be absolute pressure sensors or various types of relative or differential pressure sensors and may produce variable pressure sensor outputs, e.g., any detected pressure over a range of pressures, or may be binary pressure sensors and produce an output either indicative or not indicative of detected pressure.

The sensory cushioning system 200 may optionally further include one or more orientation sensors 214, e.g., an accelerometer, a gyroscope, a magnetometer, etc. As will be disclosed in detail herein, the control circuitry 206 may utilize the output from the orientation sensor 214 to adapt the enhanced wearable mobility article 102 or other mobility enhancing wearable articles disclosed herein to the way the enhanced wearable mobility article 102 is being used by the user. In various examples, control circuitry 206 may utilize the output of the orientation sensor 214 in conjunction with the pressure sensors 204 for such determinations.

Figure 4A:
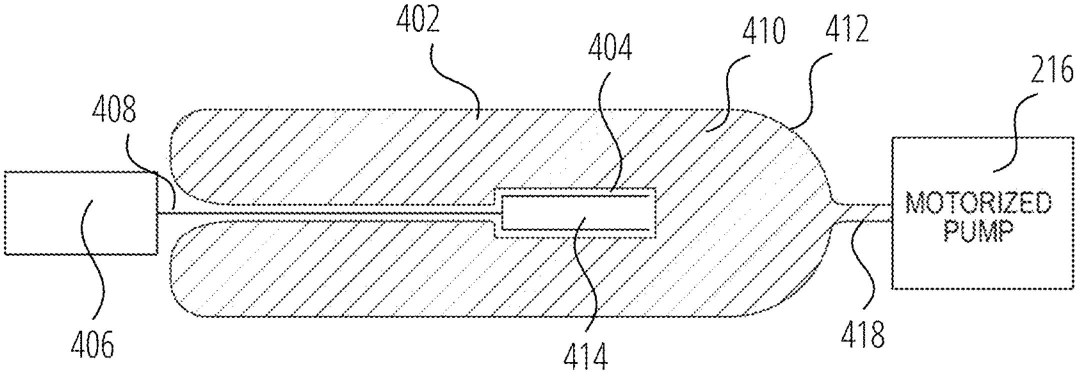
FIGS. 4A and 4B are side and perspective depictions, respectively, of a sensory cushioning system, in an example embodiment.

The sensory cushioning system 200 may further optionally include a motorized pump 216. As will be disclosed in detail herein, the motorized pump 216 may, in various examples, be utilized to increase or decrease pressure in an airbag 402 (FIG. 4A). In such examples, the control circuitry 206 may utilize data from the pressure sensors 204 and/or the orientation sensor 214 to increase or decrease the air pressure within the airbag 402.

The haptic devices 202 may include any devices which induce or otherwise create a physical sensation discernable or configured to be discernable to a user of the sensory cushioning system 200. In various examples, the haptic device 202 may be a motor, including a motor of the motorized pump 216, or a vibratory motor that does not operatively drive any other components, a resistance mechanism, a resonance mechanism, and the like. Additionally or alternatively, the haptic devices may be the same as or related to haptic devices disclosed in U.S. Pat. No. 10,055,948, APPAREL WITH ULTRASONIC POSITION SENSING AND HAPTIC FEEDBACK FOR ACTIVITIES, Kim, issued Aug. 21, 2018, and U.S. Pat. No. 10,409,961, PREDICTABLE AND ADAPTIVE PERSONAL FITNESS PLANNING, Flaherty, issued Sep. 10, 2019, which are incorporated herein by reference in their entirety. As will be disclosed herein, the haptic devices 202 may, in various examples, be positioned within the airbag 402 or external to the airbag 402, resulting in different considerations for the needed amplitude or strength of the resultant haptic signal, i.e., when the haptic device 202 is within the airbag 402 the haptic signal may need to be relatively stronger than when the haptic device 202 is external to the airbag 402.

As further noted in U.S. Pat. No. 10,055,948, the haptic devices 202 may be or may include ultrasonic positioning sensors that allow for the haptic device 202 to determine their relation with respect to one another. In various examples, the control circuitry 206 may utilize the data generated by the ultrasonic positioning sensors as part of or in addition to the orientation sensors 214 to help determine the orientation or attitude of the sensory cushioning system 200 and the enhanced wearable mobility article 102 more generally.

The control circuitry 206 may further include a user interface. The user interface may include one or more individual user interfaces that may combine to allow one or more users to control or otherwise adjust the performance of the sensory cushioning system 200. The user interface may utilize specific user interface components, such as buttons or other touch interface or the like which may be integrated with the sensory cushioning system 200 directly, e.g., placed on the enhanced wearable mobility article 102 that may be accessible to the wearer or to another user while the enhanced wearable mobility article 102 is being utilized. Additionally or alternatively, the user interface may further utilize the communication module 210 to receive instructions and send information to a remote system, e.g., remote system 1404 (FIG. 14), such as a smartphone, tablet computer, laptop computer, server, or the like. Moreover, the user interface may utilize components of the sensory cushioning system 200 that are directed to other functions, e.g., the pressure sensor 204 or the orientation sensor 214, to provide for gesture control of the sensory cushioning system 200. In various examples, gesture control of the sensory cushioning system 200 may be implemented according to the mechanisms disclosed in U.S. Pat. No. 11,071,344, MOTORIZED SHOE WITH GESTURE CONTROL, Beers, issued Jul. 27, 2021; U.S. Pat. No. 11,243,611, GESTURE RECOGNITION, Goel, issued Feb. 8, 2022; U.S. Patent Application Publication No. 2022/0193490, GESTURE RECOGNITION DEVICE FOR FOOTWEAR MOTOR ACTUATION, Ghiotto, filed on Dec. 20, 2021; and U.S. Pat. No. 9,002,680, FOOT GESTURES FOR COMPUTER INPUT AND INTERFACE CONTROL, Nurse, issued Apr. 7, 2015, all of which are incorporated by reference herein in their entirety.

The enhanced wearable mobility article 102, or other wearable articles disclosed herein, may utilize covers or other similar devices to protect or contribute to the concealment of various functional components of the enhanced wearable mobility article 102. In various examples, such covers may incorporate further functional elements related to the operation of the enhanced wearable mobility article 102 and/or the sensory cushioning system 200 generally. In various examples, covers or attachments, such as those disclosed in U.S. Patent Application Publication No. 2022/0211140, SYSTEMS AND METHODS FOR CUSTOMIZING ARTICLES OF FOOTWEAR AND PROVIDING DIGITAL OR METAVERSE CAPABILITIES, Vasilev, filed Jan. 5, 2022; U.S. Pat. No. 9,326,566, FOOTWEAR HAVING COVERABLE MOTORIZED ADJUSTMENT SYSTEM, Beers, issued May 3, 2016; and U.S. Patent Application Publication No. 2024/0012915, WEARABLE ARTICLE WITH INTEGRATED DISPLAY FOR DISPLAYING CRYPTOGRAPHICALLY SECURED DIGITAL IMAGES, Andon, filed Sep. 19, 2023, which are incorporated by reference in their entirety, may protect components of the enhanced wearable mobility article 102 while also providing dynamic custom adaptation ability to the wearer of the enhanced wearable mobility article 102 and/or providing aesthetic improvement to the enhanced wearable mobility article 102.

Figure 3:
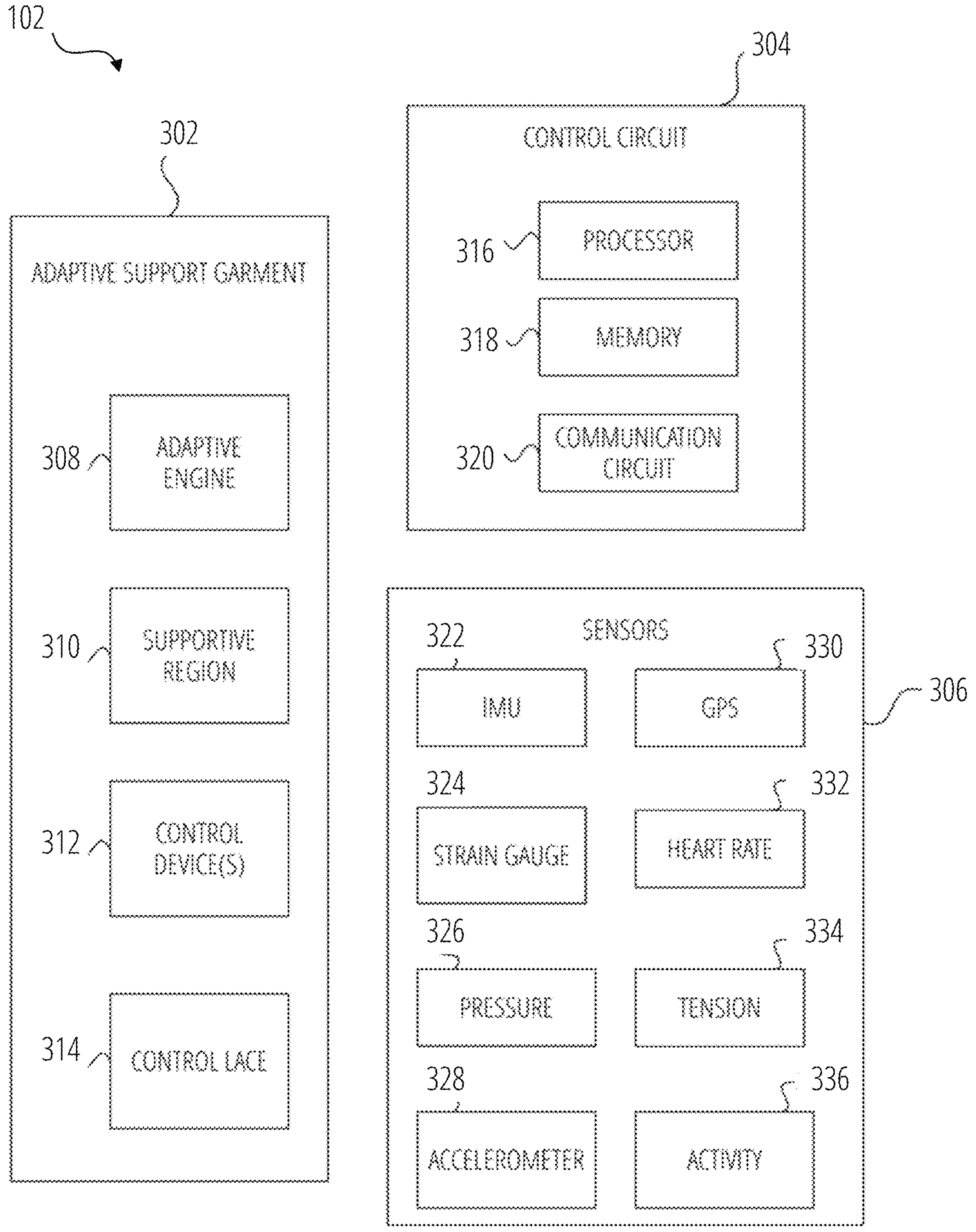
FIG. 3 is a block diagram illustrating components of an enhanced wearable mobility article, according to some example embodiments.

FIG. 3 is a block diagram illustrating components of the enhanced wearable mobility article 102, according to some example embodiments. While the enhanced wearable mobility article 102 is discussed, it is to be recognized and understood that in various examples of the enhanced wearable mobility article 102, not necessarily every component illustrated is included. Moreover, the block diagram may be applicable to any suitable enhanced wearable mobility article and may include or supplement components of the sensory cushioning system 200 illustrated in FIG. 2. Further details of an example alternative enhanced wearable mobility article which may be enabled by the block diagram may be seen in U.S. Patent Application Publication No. 2022/0338558, DIGITAL CONTROL SYSTEMS AND METHODS FOR ADAPTIVE APPAREL, Hopkins, filed Apr. 21, 2022, which is incorporated by reference herein in its entirety.

In this example, the includes components such as adaptive support garment 302, control circuitry 304, and activity sensors 306. The adaptive support garment 302 may include an adaptive engine 308, an adaptive supportive region 310, one or more control device 312, and a control lace 314. The adaptive engine 308 may be integrated within the adaptive support garment 302 or the enhanced wearable mobility article 102 more generally. The adaptive support garment 302 can include an adaptive supportive region 310. The adaptive supportive region 310 includes one or more control laces 314 configured to selectively become inelastic and/or elastic and a control device 312, e.g., a controller or other control circuitry, that can generate and/or provide signals that control actuation of the control laces 314.

The control lace 314 can include an indicator comprising a haptic feedback device, light source, or other interface means that can indicate whether the control lace and/or support garment control device 312 is engaged or disengaged, or to indicate a degree to which the control device 312 is engaged.

The control circuitry 304 includes, in this example, a processor 316, a computer readable memory device 318, and a communication circuit 320. As discussed above, in some examples the control device 312 can be integrated within a smartphone, smart watch or other wearable device or mobile device. In those examples, the control device 312 is embodied within a software application running on an operating system (e.g., iOS or Android) for the smart watch or smartphone hardware. Accordingly, the processor 316 and computer readable memory device 318 would be part of the smartphone or smart watch. In the illustrated example, the control device 312 is a standalone device or integrated into the adaptive support garment 302.

The processor 316 accesses instructions stored in the computer readable memory device 318 to process activity data received over the communication circuit 320. The activity data can also be stored on the computer readable memory device 318 at least during processing operations. The processor 316 also processes instructions that enable it to generate and transmit, over the communication circuit 320, commands to the adaptive engine 308. The commands communicated to the adaptive engine 308 control activation of the adaptive engine 308 to change support characteristics of the adaptive support garment 302.

The control device 312 receives activity data from activity sensors 306. In this example, activity sensors 306 can include any combination of an inertial measurement device 322, a strain gauge 324 (e.g., a capacitance-based strain gauge configured to measure displacement information), a pressure sensor 326, an accelerometer 328, a global positioning system 330, a heart rate sensor 332, a tension sensor 334, and among other sensors capable of producing data indicative of a user's activity level (e.g., an activity sensor 336). The activity sensors 306 can include any combination of the listed sensors and transmits the produced activity data to the control device 312 over a wireless communication link, such as Bluetooth® LE (Low Energy). Additionally, as alluded to above, the components of the enhanced wearable mobility article 102 discussed above can be distributed in any combination across devices including a smart watch, a smartphone, a footwear assembly, or an adaptive support garment (e.g., integrated into an adaptive engine).

Figure 4B:
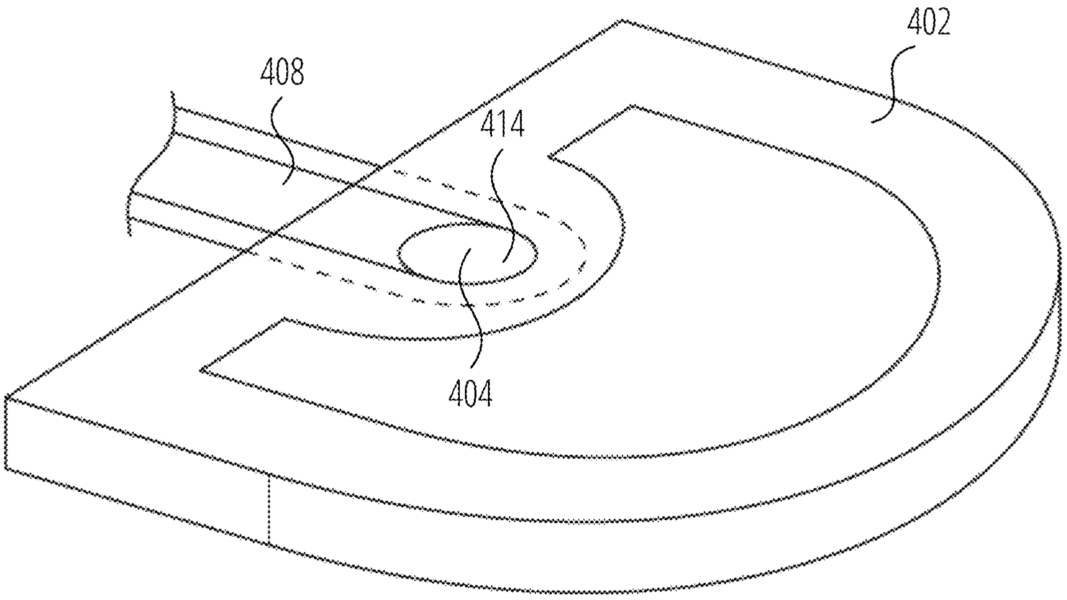

FIGS. 4A and 4B are side and perspective depictions, respectively, of the sensory cushioning system 200, in an example embodiment. In the illustrated example, the sensory cushioning system 200 includes an airbag 402, an internal electronic assembly 404, an external electronic assembly 406, and a wired interconnect 408 operatively coupling the internal electronic assembly 404 to the external electronic assembly 406. Alternatively, the external electronic assembly 406 and/or the wired interconnect 408 may be omitted and the sensory cushioning system 200 may communicate wirelessly or not at all with outside systems.

The internal electronic assembly 404 and the external electronic assembly 406 may combine to include all of the electronic components of the sensory cushioning system 200 described in FIG. 2. Consequently, where the external electronic assembly 406 is omitted the internal electronic assembly 404 may include all of the electronic components of the sensory cushioning system 200. In examples where the external electronic assembly 406 is included, each electronic assembly 404, 406 may include whatever components of the sensory cushioning system 200 that may advantageously be included on each electronic assembly 404, 406.

In various examples, the pressure sensors 204 and control circuitry 206 are included as part of the internal electronic assembly 404 while some or all of the haptic devices 202, the power source 208, and the communication module 210 are included as part of the external electronic assembly 406. Alternatively, the external electronic assembly 406 may include only the communication module 210. Each of the internal electronic assembly 404 and the external electronic assembly 406 may include conventional electronic components to facilitate the inclusion and operable coupling of the various electronic components, including a circuit board, e.g., a flexible circuit board as desired.

The wired interconnect 408 allows for a strong interconnection between the internal electronic assembly 404 and the external electronic assembly 406 which is tolerant to shear forces which may be experienced with respect to wearable devices. The inclusion of the wired interconnect 408 with the airbag 402 may be made without compromising the perimeter seal of the airbag 402, reducing the risk of leaks. In various examples, the internal electronic assembly 404, external electronic assembly 406, and wired interconnect 408 may be made from a thermoplastic polyurethane (TPU) bond, e.g., through radio frequency (RF) bonding or thermal welding, and includes features that may be resilient to the relatively large sheer forces that may be experienced in a wearable article while maintaining electrical connection using normal forces. In such examples, the bond to the internal electronic assembly 404 and the external electronic assembly 406 is separate from the perimeter bond of the airbag 402, thereby preventing airbag leakage outside of ordinary footwear airbag parameters. Additionally or alternatively, conductive elements may be disposed on the airbag 402 to provide electrical connection between the electronic components of the sensory cushioning system 200 also disposed on the airbag 402 on the internal electronic assembly 404. While TPU will be discussed in detail herein, it is to be recognized and understood the principles discussed with respect to TPU will apply as well to any other suitable material or combination of materials.

The airbag 402 may incorporate various design elements, as disclosed herein. For example, the airbag 402 may include an airbag substrate forming an air bladder comprising two plies of polymeric membrane, as is described in U.S. Pat. No. 5,802,739 to Potter et al. In another embodiment, a four-ply air bladder may be used, as is described in U.S. Pat. No. 6,402,879 to Tawney et al. In yet another embodiment, a fabric cushioning element may be used, as is described in U.S. Pat. No. 8,764,931 to Turner. The entire contents of U.S. Pat. Nos. 5,802,739; 6,402,879; and 8,764,931 are hereby incorporated by this reference for all purposes. In yet other embodiments, a bladder may be filled with other gases, such as nitrogen, helium or so-called dense gases such as sulfur hexafluoride, a liquid, or gel. In various examples, notwithstanding the material disclosed in the U.S. Pat. Nos. 5,802,739; 6,402,879; and 8,764,931, the airbag substrate may be formed in part from (TPU) and according to the principles disclosed in those patents. In various examples, TPU forms at least one ply of the airbag substrate and/or is a blended component of one or more plies.

In the illustrated example, the airbag 402 includes fibers 410 extending between the interior surfaces 412 of the airbag 402. The fibers 410 may improve structural resilience of the airbag 402. The airbag 402 may be implemented as disclosed in U.S. Pat. No. 8,479,412, TETHERED FLUID-FILLED CHAMBERS, Peyton et al., filed Dec. 3, 2009, and U.S. Patent Publication No. 2019/0365043, SPACER TEXTILE MATHERIALS AND METHODS FOR MANUFACTURING THE SPACER TEXTILE MATERIAL, Hazenberg et al., filed Aug. 19, 2019, both of which are incorporated herein by reference in their entirety.

The airbag 402 may be formed according to principles and processes described with respect to U.S. Patent Application Publication No. 2020/0260819, MIDSOLE SYSTEM WITH GRADED RESPONSE, Case et al., filed on May 5, 2020, and U.S. application Ser. No. 17/207,322, Elder et al., FOOTWEAR WITH FLUID-FILLED BLADDER, filed on Mar. 19, 2021, which claims the benefit of priority to U.S. Provisional Patent Application No. 63/030,344, all of which are incorporated by reference here in in their entirety. In general, the processes described above provide for the formation of a pocket 414 within the airbag 402. The internal electronic assembly 404 is positioned or seated in the pocket 414 and the airbag is melted in a melt region to seal the airbag 402 around the pocket 414 and provide environmental isolation for the internal electronic assembly 404. As a result, force placed on the airbag 402 generally may be imparted on and sensed by the pressure sensors 204 included in the internal electronic assembly 404. This process is described in further detail in U.S. Patent Application Publication No. 2021/0368925, FOOTWEAR AIRBAG WITH FLEXIBLE ELECTRONIC INTERCONNECT, Schneider, filed May 28, 2021, which is incorporated by reference herein in its entirety. While the airbag 402 is described with respect to the process noted above, it is noted and emphasized the airbag 402 be formed according to the processes described in U.S. Patent Application Publication No. 2021/0368925.

The illustrated example of the airbag 402 further includes an optional channel 418 operatively coupled to the optional motorized pump 216. The channel 418 and motorized pump 216 are configured to allow the pressure within the airbag 402 to be increased or decreased as desired. In various examples, the airbag 402 may have a variable pressure level according to any of a variety of mechanisms known in the art, including those disclosed in U.S. Pat. No. 10,575,589, ELECTRONICALLY CONTROLLED BALDDER ASSEMBLY, Molyneux, issued Mar. 3, 2020; U.S. Patent Application Publication No. 2020/0163411, ELECTRONICALLY CONTROLLED BALDDER ASSEMBLY, Molyneux, filed on Jan. 29, 2020; U.S. Pat. No. 6,430,843, DYNAMICALLY-CONTROLLED CUSHIONING SYSTEM FOR AN ARTICLE OF FOOTWEAR, Potter, issued on Aug. 13, 2002; U.S. Patent Publication No. 2007/0006489, CONTROL SYSTEMS AND FOOT-RECEIVING DEVICE PRODUCTS CONTAINING SUCH SYSTEMS, Case, filed Jul. 11, 2005; and U.S. Patent Application Publication No. 2004/0177531, INTELLIGENT FOOTWEAR SYSTEMS, DiBenedetto, filed Mar. 10, 2003; and U.S. Pat. No. 11,825,905, FOOT SUPPORT SYSTEMS INCLUDING FLUID MOVEMENT CONTROLLERS AND ADJUSTABLE FOOT SUPPORT PRESSURE, Browne, issued Nov. 28, 2023, all of which are incorporated by reference herein in their entirety.

Additionally or alternatively, while the airbag 402 is described as being filled with air, it is to be recognized and understood that the airbag 402 may be filled with any suitable gas, fluid, gel, or other substance. For instance, the airbag 402 may be filled with rheological or other variable viscosity fluid, as disclosed in U.S. Pat. No. 9,198,478, SUPPORT MEMBERS WITH VARIABLE VISCOSITY FLUID FOR FOOTWEAR, Meschter, issued Dec. 1, 2015, which is incorporated by reference herein in its entirety. Additionally or alternatively, the substance incorporated in the airbag 402 may be dynamically controllable as disclosed herein according to any suitable mechanism, e.g., as disclosed in U.S. patent application Ser. No. 18/893,509, ADJUSTABLE FOOT SUPPORT SYSTEMS INCLUDING FLUID-FILLED BLADDER CHAMBERS; U.S. Pat. No. 9,743,712, SOLE STRUCTURE WITH ELECTRICALLY CONTROLLABLE DAMPING ELEMENT, Orand, issued Aug. 28, 2017; or U.S. Pat. No. 11,096,445, FOOTWEAR INCLUDING INCLINE ADJUSTER, Walker, issued Aug. 24, 2021, all of which are incorporated by reference herein in their entirety. Moreover, the airbag 402 as filled with air, and the sensory cushioning system 200 more generally, may work in conjunction with any suitable fluid-filled system, including those disclosed herein. In various examples, the sensory cushioning system 200 may either control the fluid-filled system or may be controlled along with the fluid-filled system in order to provide enhanced reactivity and responsiveness to wearer activity.

Figure 5:
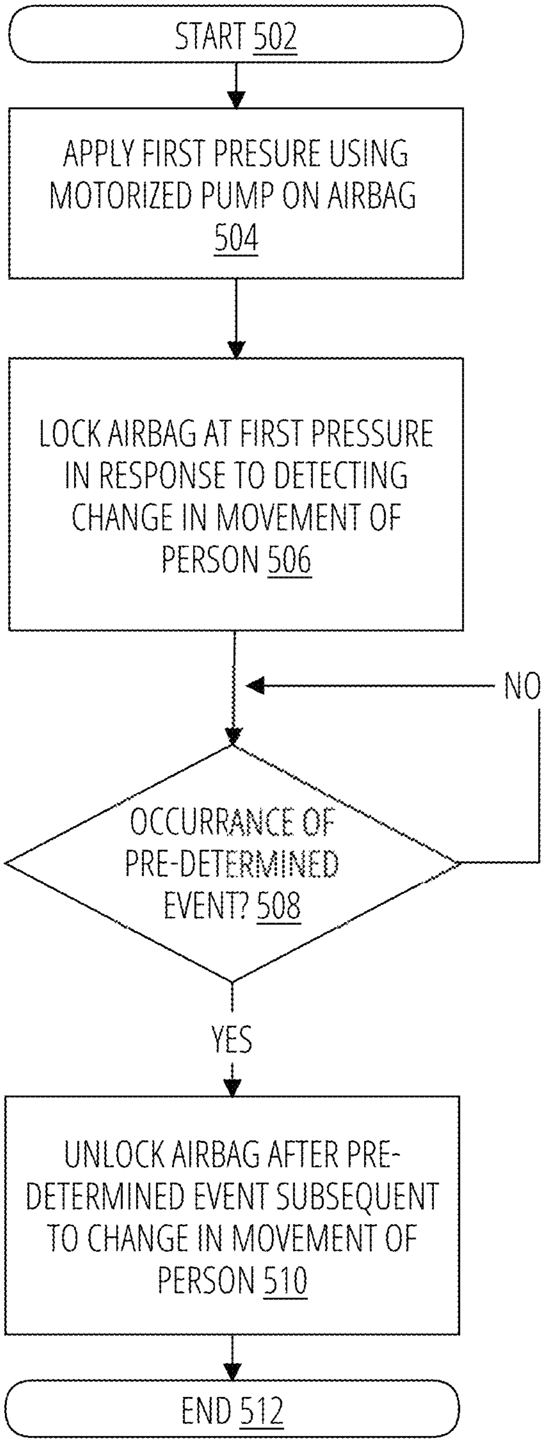
FIG. 5 is a flowchart illustrating an example method for selectively controlling a portion of a sensory cushioning system, according to an example embodiment.

FIG. 5 is a flowchart illustrating an example method for selectively controlling a portion of a sensory cushioning system 200, according to an example embodiment. The method can be performed by any of the control mechanism discussed herein in cooperation with the enhanced wearable mobility article 102 discussed above. The method may be performed by the control circuitry 206 of the sensory cushioning system 200 or by any suitable control In some embodiments, the method includes operations for providing dynamic support for an appendage of a person. The method begins at 502 and proceeds to operation 504 by applying a first pressure using the motorized pump 216. At operation 506, the control circuitry 206 holds the pressure at the first pressure in response to detecting a change in movement of the person. In some examples, a movement input is detected and/or received from a sensor adapted for monitoring movements of the person, e.g., the pressure sensors 204, the orientation sensor 214, one or more of the activity sensors 306, etc. The output from the sensor is evaluated to detect the change of movement of the person. The output from the sensor may be evaluated to predict a future motion of the person to preemptively apply the pressure using the motorized pump 216. Additionally, the output of the sensor may be evaluated to determine a duration of time for the first pressure to remain locked. Based on the output of the sensor, a direction and/or acceleration rate of the person can be determined. The acceleration and/or direction may be used to adjust the first tension according to the direction and acceleration of the person.

At operation 508, a determination is made whether a pre-determined event subsequent to the change in movement of the person has occurred. If yes, the method continues at operation 510 to change the pressure in the airbag 402.

In some examples, the pre-determined event includes expiration of a time delay since locking the pressure at the first pressure. In other examples, the pre-determined event includes receiving an indication (e.g., from a sensor) that the movement of the person has changed in acceleration, direction, and/or frequency. In yet other examples, the pre-determined event can include a pressure in the airbag 402 meeting, exceeding, or otherwise traversing a predetermined value or relative change in pressure.

After the airbag 402 is unlocked at operation 510, in some examples, the method includes applying a second pressure from the motorized pump 216, the second pressure being either higher or lower the first pressure. The airbag 402 may be locked at the second pressure to restrict a change in pressure in response to detecting a second change in movement of the person. The second change in movement of the person may include an acceleration of the person in one or more directions. The airbag 402 is unlocked after a second pre-determined event subsequent to the second change in movement of the person. The second pre-determined event may in some embodiments be the same pre-determined event that was detected to unlock the support garment control device at the first tension.

The method may end at operation 512 or in some examples, repeat as determined necessary to provide dynamic support for a wearer while the wearer is in motion.

Figure 6:
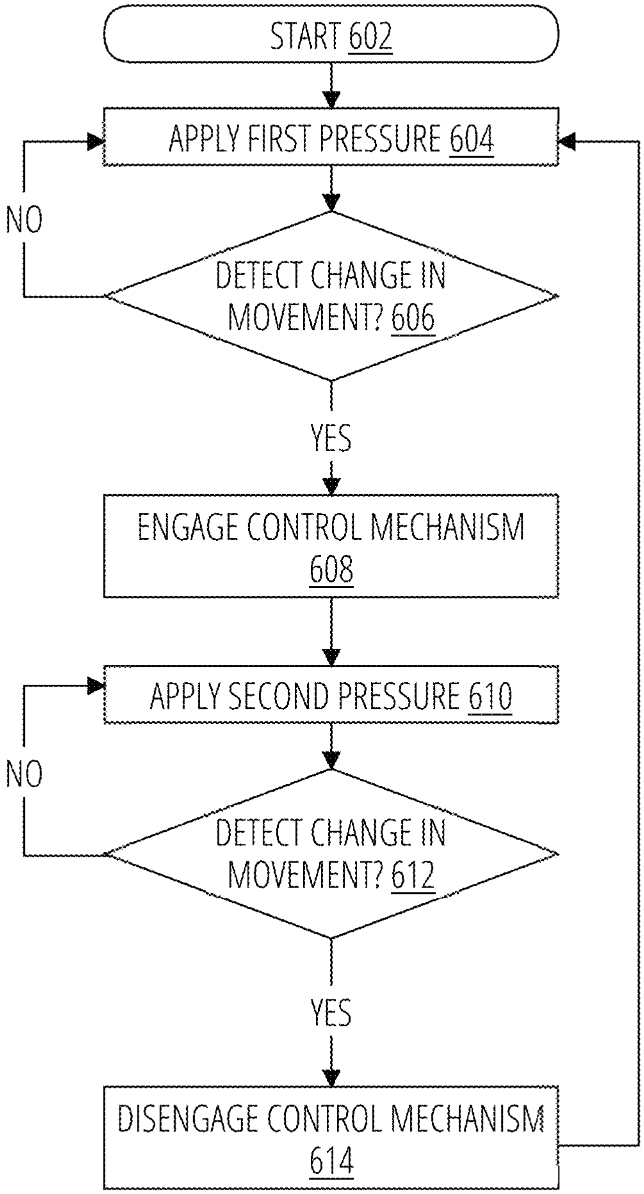
FIG. 6 is a flowchart illustrating an example method for controlling a sensory cushioning system, according to an example embodiment.

FIG. 6 is a flowchart illustrating an example method for controlling the sensory cushioning system 200, according to an example embodiment. The method can be performed by any of the control mechanisms discussed herein.

In an example, the method includes operations for applying a first pressure to the airbag 402 at operation 604, engaging a control mechanism of control circuitry 206 at 608, applying a second pressure on the airbag 402 at 610, and disengaging the control mechanism with the control circuitry 206 at 614. In this example, the method begins as a user engages in an impact oriented physical activity and continues during the entire impact oriented physical activity. At 604 the method begins with the control mechanism of the control circuitry 206 applying a first pressure on the airbag 402 with the motorized pump 216 that is coupled to an enhanced wearable mobility article 102.

At 606 the control circuitry 206 determines if a change of movement of the wearer has occurred sufficient to necessitate a reaction in the performance of the enhanced wearable mobility article 102 and/or the pressure in the airbag 402, e.g., based on the output from the pressure sensor 204, the orientation sensor 214, and/or the activity sensors 306. If so, the method proceeds to engage the control mechanism in the control circuitry 206 at 608. If not, the method returns to 604.

At 610, the motorized pump 216 causes the pressure in the airbag 402 to increase or decrease as appropriate given the output of the various sensors.

At 612, the control circuitry 206 monitors the various sensors and either detects a further change in movement such that the wearer has returned their activity or movement to a level consistent with the first pressure, in which case the method proceeds to 614, or does not, in which case the method proceeds back to 610. At 614, the control circuitry 206 disengages the control mechanism and returns the airbag 402 to the first pressure at 604 by operating the motorized pump 216.

Figure 7:
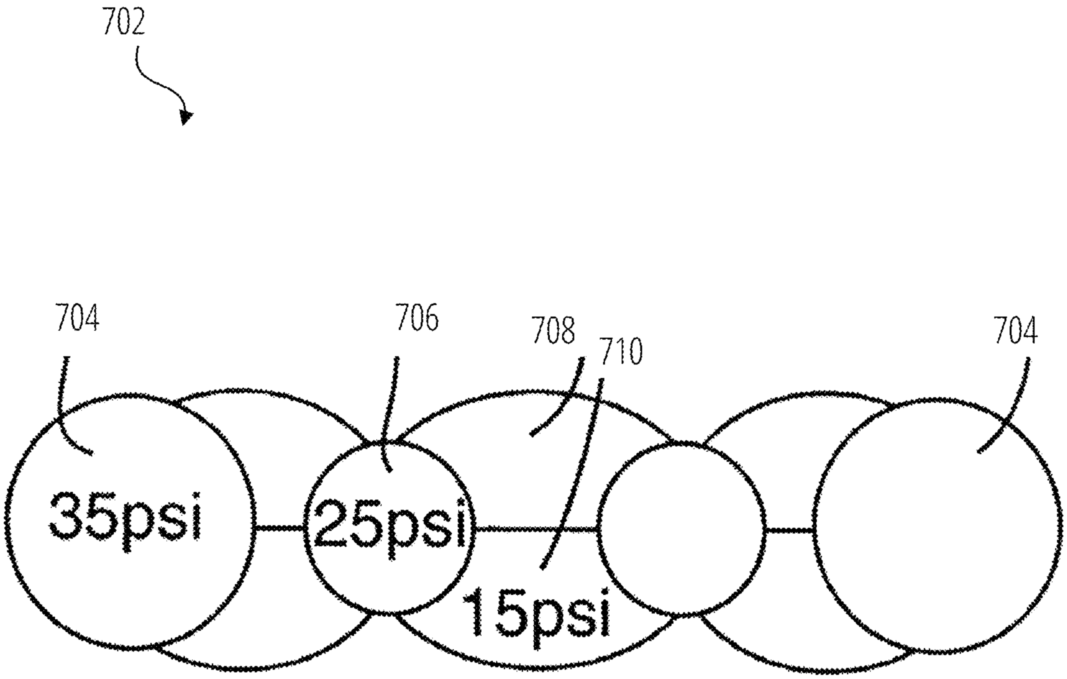
FIG. 7 is a diagram of a multi-chamber airbag, in an example embodiment.

FIG. 7 is a diagram of a multi-chamber airbag 702, in an example embodiment. The multi-chamber airbag 702 may be implemented instead of the single-chamber airbag 402 in the sensory cushioning system 200. The multi-chamber airbag 702 includes side chambers 704 and central chambers 706 formed from inner film layers, while top chambers 708 and bottom chambers 710 are formed between an outer film layer and an adjacent inner film layer. In such an example, various chambers are enabled to be pressurized to different pressures. In this example, the side chambers 704 are pressurized to thirty-five (35) pounds per square inch (psi), the central chambers 706 are pressurized to twenty-five (25) psi, and the top chambers 708 and bottom chambers 710 are pressurized to fifteen (15) psi. In this cushioning profile, the lower pressure top chamber 708 and bottom chamber 710 will provide a soft point of purchase feel and general cushioning for light loads. When a high impact load is applied, the high-pressure central chambers 706 provide the needed dampening of the load, and the higher pressure side chambers 704 will stabilize the wearer by providing a stiffer response at the sides to, e.g., cradle the curved metatarsal head of a wearer's foot. This profile illustrates an example of bladder construction and pressurization to provide anatomically coupled, regionalized cushioning for a wearer's foot.

As noted, the multi-chamber airbag 702 may be applied within the sensory cushioning system 200 in place of the single-chamber airbag 402. As such, some or all of the chambers 704, 706, 708, 710 may be operatively coupled to a motorized pump 216 so as to increase or decrease the pressure within the respective chamber 704, 706, 708, 710. Consequently, the multi-chamber airbag 702 may be highly adaptable to the circumstances of the wearer of the enhanced wearable mobility article 102. Details of the construction of the multi-chamber airbag 702 may be found in U.S. Pat. No. 6,402,879, which has been incorporated by reference in its entirety.

Figure 8:
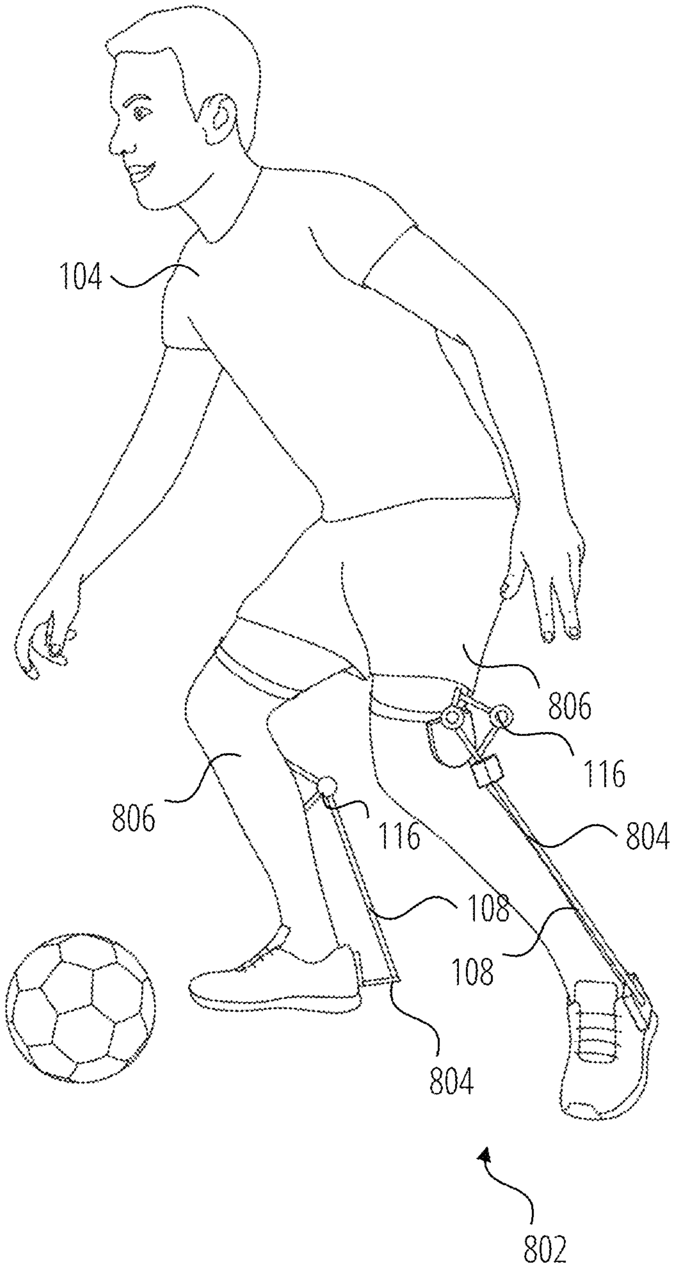
FIG. 8 is a set of enhanced wearable mobility articles being used by a wearer, in an example embodiment.

FIG. 8 is a set of enhanced wearable mobility articles 802 being used by a wearer 104, in an example embodiment. The set of enhanced wearable mobility articles 802 includes two mobility-enhancing wearable articles 804, each configured to be secured to a leg 806 of a wearer 104. The set of enhanced wearable mobility articles 802 may be configured to coordinate movement between the two mobility-enhancing wearable articles 804 through the use of electronic communication between the two mobility-enhancing wearable articles 804, in various examples wireless communication. Alternatively, each mobility-enhancing wearable article 804 may individually sense and assess the state of the leg 806 to which it is secured and enhance the mobility of the leg without regard to the operation of the other mobility-enhancing wearable article 804 of the set of enhanced wearable mobility articles 802.

In various examples, the set of enhanced wearable mobility articles 802 are therefore configured specifically to provide enhanced mobility for leg-specific contexts but otherwise incorporate similar elements to those of the enhanced wearable mobility article 102, including a rigid frame 108 and at least one joint 116. In the illustrated example, the wearer 104 is playing soccer/football and the set of enhanced wearable mobility articles 802 may be configured to allow a wearer 104 who has impaired mobility to play the game in the first place through the use of sensors, motors and the like while also providing sensory enhancement for the wearer 104 through haptic feedback or may enhance the ability of a player to make long passes or kick at high velocity. Additionally or alternatively, the set of enhanced wearable mobility articles 802 may enhance the capacity of the wearer 104 to run, jump, change direction, or engage in other mobility-related action rather than to provide such function in the first place. Thus, in various examples, the set of enhanced wearable mobility articles 802 may allow an otherwise ordinary wearer 104 to, e.g., dunk a basketball who would not ordinarily be able to do so.

While a set of enhanced wearable mobility articles 802 is illustrated, it is to be recognized and understood that the wearer 104 may optionally only wear a single mobility-enhancing wearable article 804 rather than the set of enhanced wearable mobility articles 802, e.g., where the wearer 104 has an injury or reduced mobility in one leg 806 compared to the other. Moreover, while the set of enhanced wearable mobility articles 802 is illustrated with respect to being wearable on the legs 806, it is to be recognized and understood that the same principles may be applied to one or more mobility-enhancing wearable articles 804 configured to be secured to and enhance the mobility of other parts of the body of the wearer 104, including but not limited to the arms, back, or head and neck of the wearer 104. In such examples, the set of enhanced wearable mobility articles 802 may include such other mobility-enhancing wearable articles 804 in addition to or instead of the leg-worn mobility-enhancing wearable articles 804 as illustrated. In various examples, all of the mobility-enhancing wearable articles 804 of the set of enhanced wearable mobility articles 802 may optionally communicate and coordinate with one another or may operate independently of one another, as described above.

Figure 9:
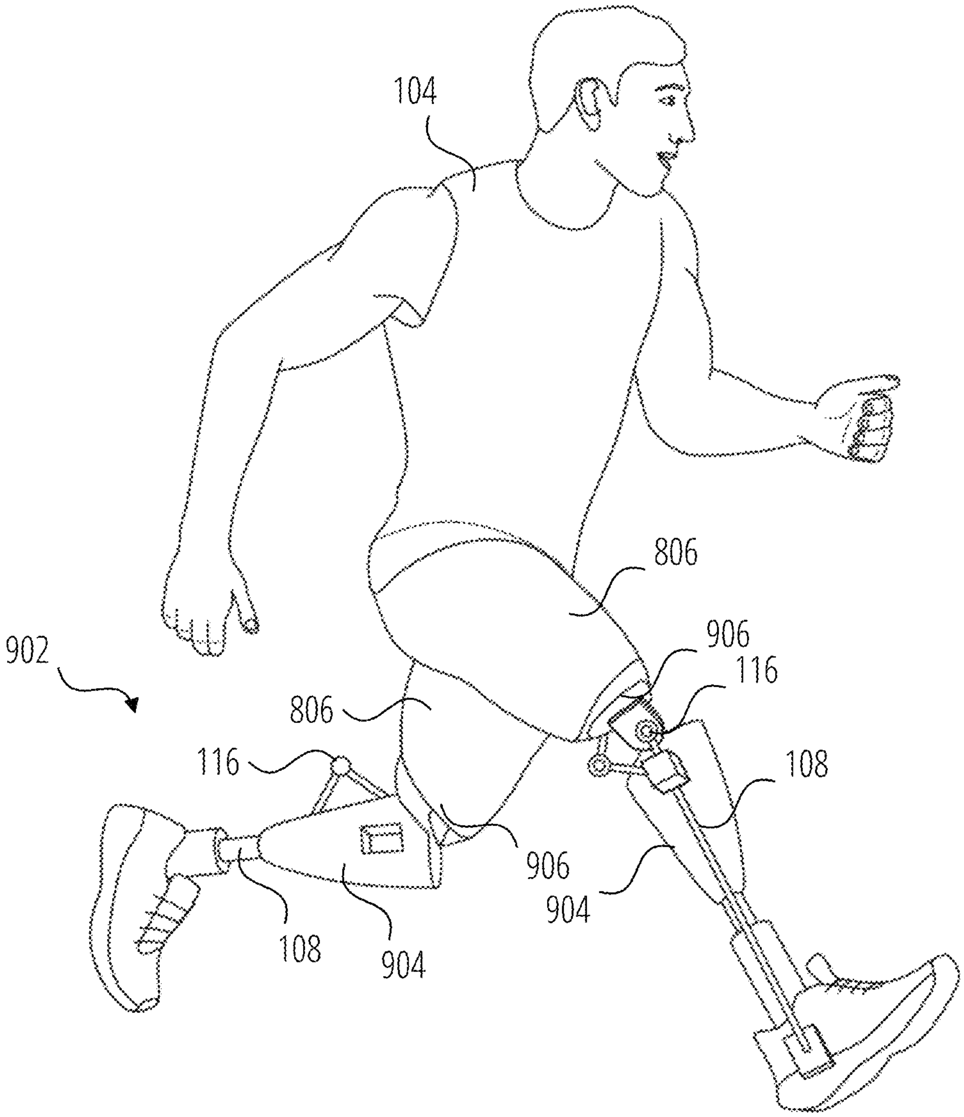
FIG. 9 is a set of enhanced wearable mobility devices being used by a wearer, in an example embodiment.

FIG. 9 is a set of enhanced wearable mobility devices 902 being used by a wearer 104, in an example embodiment. In contrast to the enhanced wearable mobility article 102 and the set of enhanced wearable mobility articles 802 of FIG. 1 and FIG. 8, respectively, which are generally related to exoskeleton functionality, the set of enhanced wearable mobility devices 902 is based on prosthetics. As illustrated, the set of enhanced wearable mobility devices 902 includes two prosthetic limbs 904, each associated with a different leg 806 of the wearer 104. However, it is to be recognized and understood that a single prosthetic limb 904 may be utilized as appropriate rather than a set of enhanced wearable mobility devices 902. Moreover, it is to be recognized and understood that the set of enhanced wearable mobility devices 902 may include any combination of enhanced wearable mobility articles 102, 804 and prosthetic limbs 904, variously acting in concert or individually.

In the illustrated example, each prosthetic limb 904 includes a rigid frame 108 and a joint 116 along with components such as a motor to move the rigid frame 108 with respect to the joint 116. As will be disclosed herein, alternative examples of a prosthetic limb do not necessarily include a joint 116 an consequently do not necessarily include a motor for motive control of the prosthetic limb 904. The prosthetic limb 904 does include at least one sensory cushion at a junction portion 906 between the prosthetic limb 904 and the leg 806 of the wearer 104.

Figure 10A:
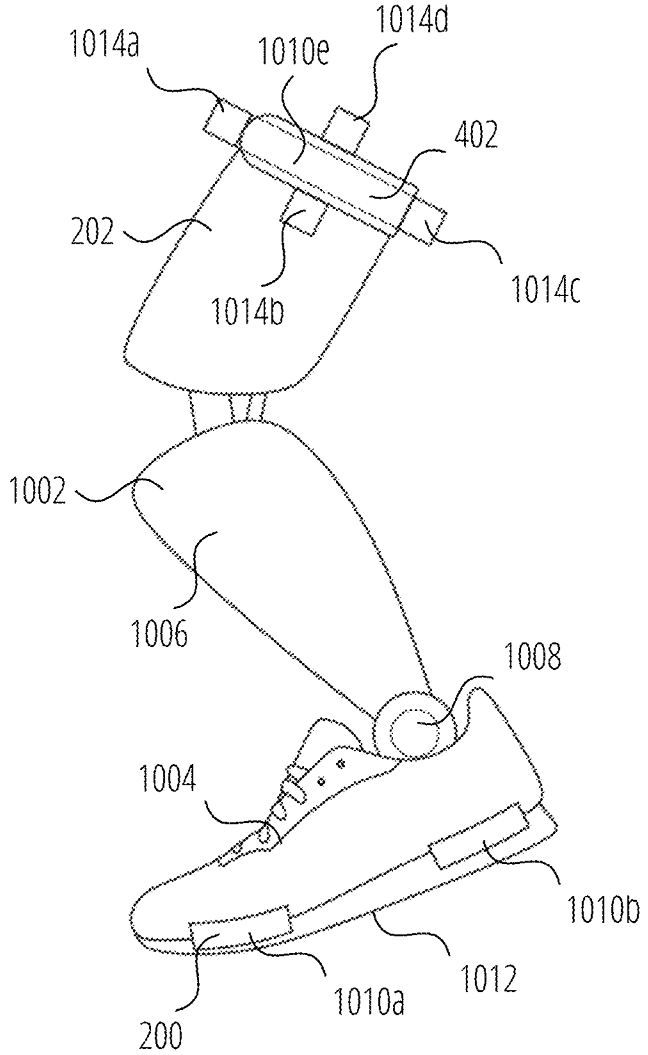
FIG. 10A and FIG. 10B are side and bottom-perspective images of an enhanced wearable mobility article, respectively, including a sensory cushioning system, in an example embodiment.
Figure 10B:
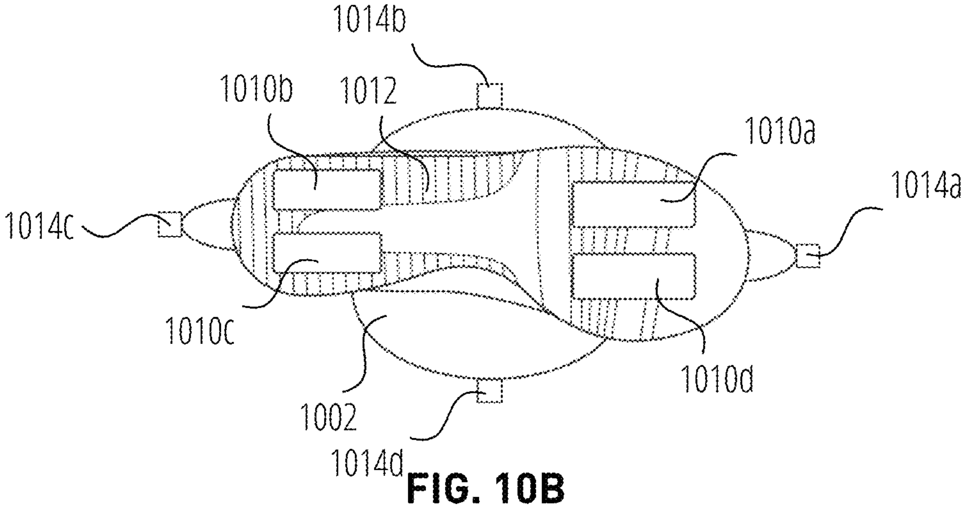

FIG. 10A and FIG. 10B are side and bottom-perspective images of an enhanced wearable mobility article 1002, respectively, including the sensory cushioning system 200, in an example embodiment. In the illustrated example, the enhanced wearable mobility article 1002 is a prosthetic limb and includes a foot portion 1004, a leg portion 1006, and a junction portion 1008 operatively coupled or coupleable between the foot portion 1004 and the leg portion 1006. The foot portion 1004 is configured to contact the ground, floor, or other related surface, e.g., in the manner of an article of footwear such as a shoe, sandal, bootie, or the like. The leg portion 1006 is configured to admit and secure or to be secured to a portion of a leg of the wearer of the enhanced wearable mobility article 1002. The junction portion 1008 is generally positioned proximate what would be an ankle of the wearer and may secure the foot portion 1004 and the leg portion 1006 in alignment with one another and/or provide physical electrical contact between components of the sensory cushioning system 200 located on the enhanced wearable mobility article 1002 and the foot portion 1004.

In the illustrated example, the enhanced wearable mobility article 1002 does not include motorized components to cause the foot portion 1004 to move with respect to the leg portion 1006 at the junction portion 1008, but it is to be recognized and understood that the enhanced wearable mobility article 1002 may be implemented with such motorized components as disclosed herein with respect to other mobility-enhancing wearable devices. The foot portion 1004, leg portion 1006, and junction portion 1008 may be formed of any material suitable for a wearable article generally, including textiles, leather, plastic or other polymers, metals, and so forth.

The enhanced wearable mobility article 1002 includes multiple sensory cushioning systems 200 positioned at various locations. The sensory cushioning systems 200 may be made as specific implementations for the purposes of this enhanced wearable mobility article 1002. As such, four separate sensory cushioning systems 200, denoted as 1010*a*, 1010*b*, 1010*c*, and 1010*d*, for the purposes of illustration, are positioned on the foot portion 1004 while one sensory cushioning system 200, denoted as 1010*e*, is positioned at a top of the leg portion 1006, i.e., to be in contact with a wearer of the enhanced wearable mobility article 1002. However, in an example, the sensory cushioning systems 200 positioned on the foot portion 1004 are equipped without haptic devices 202 but do each include at least one pressure sensor 204 while the sensory cushioning system 200 positioned on the leg portion 1006 includes four haptic devices 202 as well as at least one pressure sensor 204. It is noted that the sensory cushioning systems 200 positioned in the foot portion 1004 may optionally include a haptic device 202 but that such a haptic device 202 may be of limited or no utility given the distance of the haptic device 202 from the wearer.

In the illustrated examples, the haptic devices 202 of the sensory cushioning system 1010*e*, denoted as 1014*a*, 1014*b*, 1014*c*, 1014*d* for the purposes of illustration, are positioned exterior to the airbag 402, i.e, as part of an external electronic assembly 406 of the sensory cushioning system 1010*e*. In various examples, one or more of the haptic devices 202 may be included as part of the internal electronic assembly 404 or one or more additional haptic devices 202 may be included in the internal electronic assembly 404 in addition to the haptic devices 202 included with the external electronic assembly 406.

As illustrated, the sensory cushioning system 1010*a* is generally in a forefoot-lateral location on the ground-contacting surface 1012. The sensory cushioning system 1010*b* is generally in a backfoot-lateral location on the ground-contacting surface 1012. The sensory cushioning system 1010*c* is generally in a backfoot-medial location on the ground-contacting surface 1012. The sensory cushioning system 1010*d* is generally in a forefoot-medial location on the ground-contacting surface 1012. The haptic device 1014*a* is generally located on a front of the enhanced wearable mobility article 1002. The haptic device 1014*b* is generally located on a lateral side of the enhanced wearable mobility article 1002. The haptic device 1014*c* is generally located on a back of the enhanced wearable mobility article 1002. The haptic device 1014*d* is generally located on a medial side of the enhanced wearable mobility article 1002. Consequently, in the illustrated example the sensory cushioning systems 1010*a*, 1010*b*, 1010*c*, 1010*d* are offset relative to the haptic devices 1014*a*, 1014*b*, 1014*c*, 1014*d* with respect to the perspective of FIG. 10B with, for instance, the haptic device 1014*a* being positioned between sensory cushioning system 1010*a* and sensory cushioning system 1010*d* and sensory cushioning system 1010*c* being positioned between haptic device 1014*c* and haptic device 1014*d*, albeit with the haptic devices 1014*a*, 1014*b*, 1014*c*, 1014*d* laterally offset with respect to the sensory cushioning systems 1010*a*, 1010*b*, 1010*c*, 1010*d* along the enhanced wearable mobility article 1002 as depicted in FIG. 10A.

The number of sensory cushioning systems 200 and their respective locations provided are for illustrative purposes only. It is to be recognized and understood that more or fewer sensory cushioning systems 200 may be implemented as desired for particular example embodiments or uses of the enhanced wearable mobility article 1002 and the principles described herein generally. Moreover, the locations of the various sensory cushioning systems 200 and their respective haptic devices 202, both generally on the enhanced wearable mobility article 1002 and with respect to one another may shift or otherwise be altered. Thus, in one example, the haptic devices 1014*a*, 1014*b*, 1014*c*, 1014*d* may be shifted to vertically align with an associated sensory cushioning systems 1010*a*, 1010*b*, 1010*c*, 1010*d*, e.g., with the haptic device 1014*a* directly above the sensory cushioning system 1010*a* rather than between the sensory cushioning system 1010*a* and sensory cushioning system 1010*d* as illustrated, and so forth. Alternatively, the haptic devices 1014*a*, 1014*b*, 1014*c*, 1014*d* may be left in place and an additional haptic device may be positioned in vertical alignment with the sensory cushioning systems 1010*a*, 1010*b*, 1010*c*, 1010*d*, resulting in eight (8) total haptic devices. Additional pressure sensors may also be incorporated, e.g., at midfoot lateral and midfoot medial locations.

As noted, the sensory cushioning systems 1010*a*, 1010*b*, 1010*c*, 1010*d* are individually incorporated into the enhanced wearable mobility article 1002. In various examples not limited to the example of the enhanced wearable mobility article 1002, sensory cushioning systems 200 may be incorporated into a separate structure which may be utilized as desired in wider structures. In an example, the system of U.S. Pat. No. 9,955,749, FOOTWEAR HAVING SENSOR FEEDBACK OUTSOLE, Van Atta, issued May 1, 2018, incorporated by reference herein in its entirety, may incorporate individual sensory cushioning systems 200 in place of or in addition to individual sensory feedback members disclosed therein. In such an example, the resultant lattice structure may be incorporated separately into a conventional or off-the-shelf wearable article, e.g., an article of footwear, prosthetic, sleeve, etc.

Additionally or alternatively, the resultant lattice structure may be produced and/or sold separately to consumers or users and applied to or otherwise worn by the wearer separately from an underlying wearable article. In such an example, the lattice structure may be formed as a separate wrap-around article which may be secured to the wearer with adhesive, straps, clips, or other suitable fastener. In such an example, a wearer may wrap the structure, e.g., around an arm or leg, apply the structure to their chest, back, or head, or the like. Consequently, the wearer may receive the benefits of the sensory cushioning systems 200 without needing to rely on a wider wearable article.

While the lattice structure of Van Atta is described with particularity here, it is to be recognized and understood that the principle of incorporating sensory cushioning systems 200 into structures that are not themselves wearable articles but which are designed to be incorporated into wearable articles applies beyond the lattice structure of Van Atta. Consequently, sensory cushioning systems 200 may be formed into any of a variety of wider structures, e.g., as disclosed in U.S. Pat. No. 5,983,395, EXTRA SENSORY GLOVE, Lei; U.S. Pat. No. 8,272,149, ARTICLE OF FOOTWEAR WITH A MIDSOLE STRUCTURE, Cooper; and U.S. Pat. No. 8,516,918, SOLE SYSTEM HAVING MOVABLE PROTRUDING MEMBERS, Meschter, all of which are incorporated by reference herein in their entirety.

Figure 11:
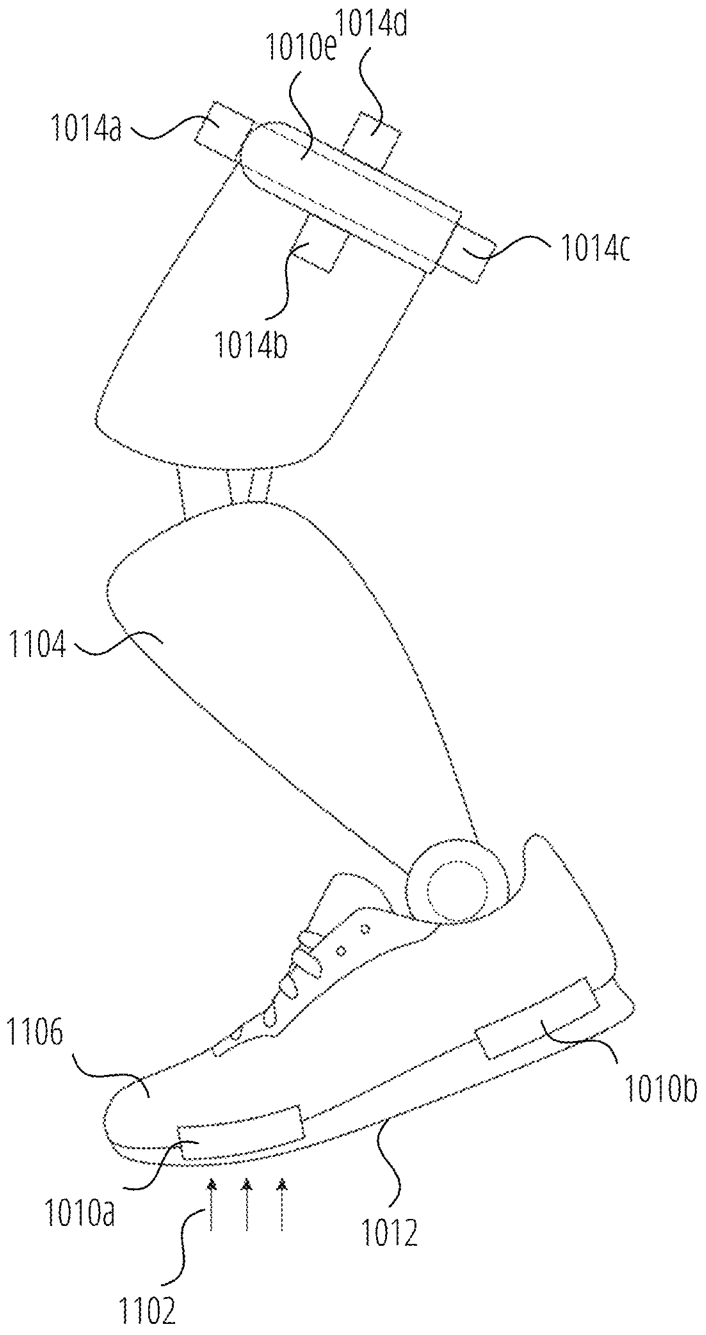
FIG. 11 is an illustration of force placed on aground-contacting surface of an enhanced wearable mobility article and how the force may translate to output from haptic devices, in an example embodiment.

FIG. 11 is an illustration of force 1102 placed on the ground-contacting surface 1012 of the enhanced wearable mobility article 1002 and how the force 1102 may translate to output from the haptic devices 1014*a*, 1014*b*, 1014*c*, 1014*d*, in an example embodiment. As a consequence of the various positions of the sensory cushioning systems 1010*a*, 1010*b* (as well as the sensory cushioning systems 1010*c*, 1010*d*, which are obscured in this depiction), force 1102 placed on the ground-contacting surface 1012 when a wearer of the enhanced wearable mobility article 1002 stands, walks, or otherwise moves around may be registered by one or more of the sensory cushioning systems 1010*a*, 1010*b*, 1010*c*, 1010*d*, which may be translated into haptic feedback by one or more of the haptic devices 1014*a*, 1014*b*, 1014*c*, 1014*d*.

In the illustrated example, the force 1102 is placed on a forefoot region 1106 of the enhanced wearable mobility article 1002 because, e.g., the wearer is walking, running, leaning forward, etc. Consequently, the weight of the wearer and the enhanced wearable mobility article 1002 will tend to bear down on the sensory cushioning system 1010*a* and lift from the sensory cushioning system 1010*b*, thereby increasing the pressure on the sensory cushioning system 1010*a* and reducing the pressure on the sensory cushioning system 1010*b*. From this, the sensory cushioning systems 200 generally may determine that the enhanced wearable mobility article 1002 is leaning forward and induce the haptic device 1014*a* to generate a haptic signal that is detectable by the wearer of the enhanced wearable mobility article 1002 to thereby alert the wearer that the enhanced wearable mobility article 1002 specifically and the wearer more generally is leaning forward. The haptic device 1014*a* may produce a stronger or weaker haptic signal depending on the amount of lean as identified by the change in the difference in the pressure as detected by the sensory cushioning system 1010*a* and sensory cushioning system 1010*b* over time or on the basis of the absolute pressure detected by both of the sensory cushioning systems 1010*a*, 1010*b*.

While the example of FIG. 11 illustrates leaning on only one axis of the enhanced wearable mobility article 1002, it is to be recognized and understood that the arrangement of the sensory cushioning systems 200 in the foot portion 1004 may provide for multi-axis sensitivity to pressure and pressure changes. Thus, for instance, referencing FIG. 10B, if the wearer leans forward and laterally then the pressure on the sensory cushioning system 1010*a* will be greater than the pressure on the sensory cushioning system 1010*b* or sensory cushioning system 1010*d*, both of which may be greater than the pressure on the sensory cushioning system 1010*c*. Based on the four different pressures or changes in relative pressure, the sensory cushioning systems 200 may thereby cause the haptic device 1014*a* and the haptic device 1014*b* to deliver haptic signals, thereby indicating to the wearer that the enhanced wearable mobility article 1002 has the forward and lateral lean.

Figure 12:
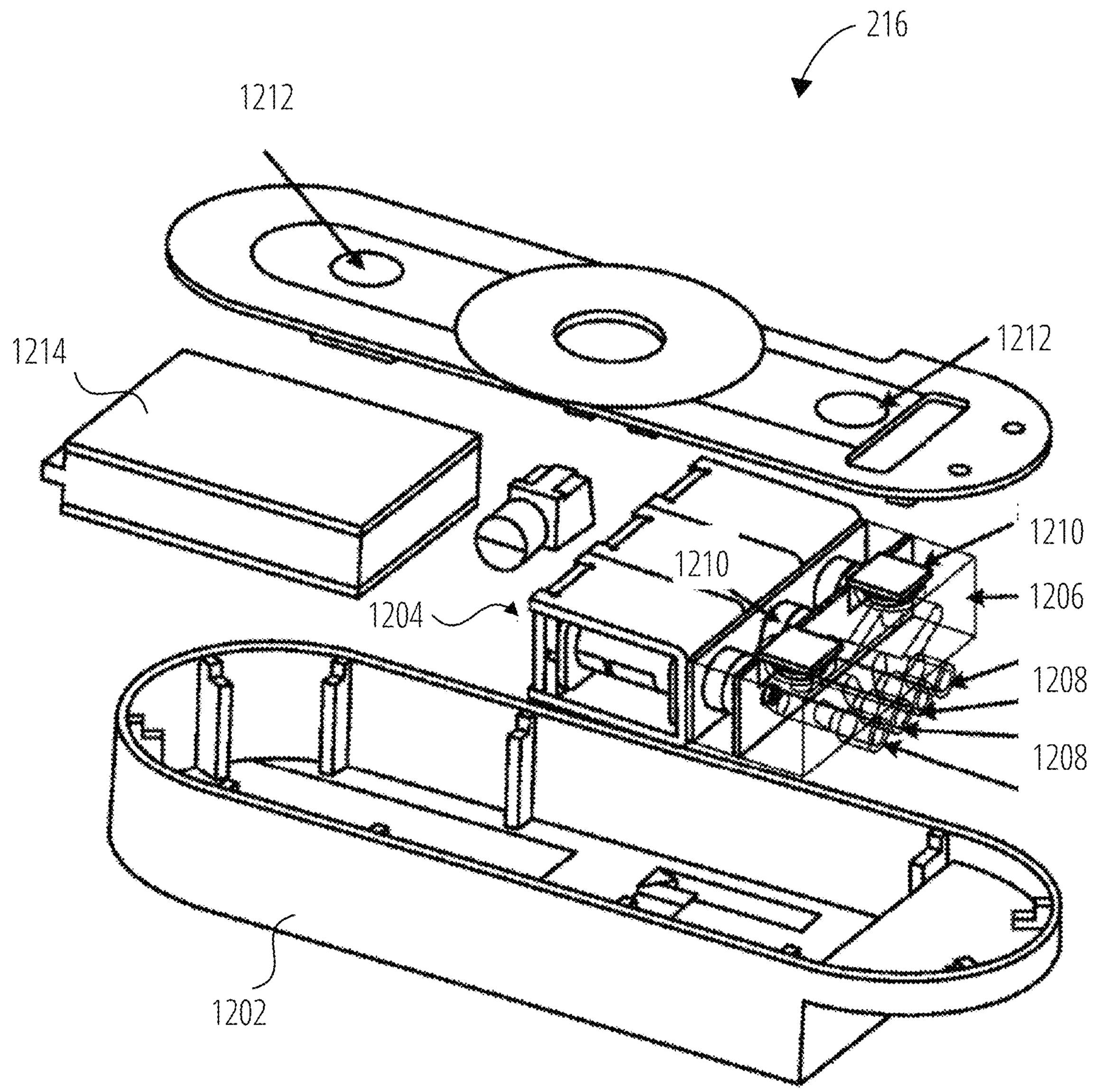
FIG. 12 is an exploded view of a motorized pump, in an example embodiment.

FIG. 12 is an exploded view of a motorized pump 216, in an example embodiment. The motorized pump 216 may be configured to be placed anywhere with respect to an enhanced wearable mobility article 102 or any other suitable article disclosed herein. As will be illustrated in FIG. 13, the motorized pump 216 may be adapted in particular to interface on an article of footwear or on a footwear portion of, e.g., the enhanced wearable mobility article 1002. The motorized pump 216 may then be connected to each of the sensory cushioning system 1010*a*, 1010*b*, 1010*c*, 1010*d* to separately control each.

The motorized pump 216 includes a housing 1202 when encloses a fluid transfer system 1204 which is coupled to a manifold 1206. The manifold 1206 includes four ports 1208, each of which is configured to be fluidly coupled to one of the sensory cushioning system 1010*a*, 1010*b*, 1010*c*, 1010*d* and to independently control the pressure within the sensory cushioning system 1010*a*, 1010*b*, 1010*c*, 1010*d*. A pair of pressure sensors 1210 help regulate the pressure within the ports 1208. A user interface in the form of buttons or switches 1212 provide direct user access to the function of the motorized pump 216 as appropriate or to obtain information from the motorized pump 216. A power source 1214, e.g., a rechargeable battery or other suitable system, provides power for the motorized pump 216. Further details of the motorized pump 216 are disclosed in U.S. Pat. No. 11,825,905, FOOT SUPPORT SYSTEMS INCLUDING FLUID MOVEMENT CONTROLLERS AND ADJUSTABLE FOOT SUPPORT PRESSURE, Browne, issued Nov. 28, 2023, which is incorporated by reference herein in its entirety.

Figure 13:
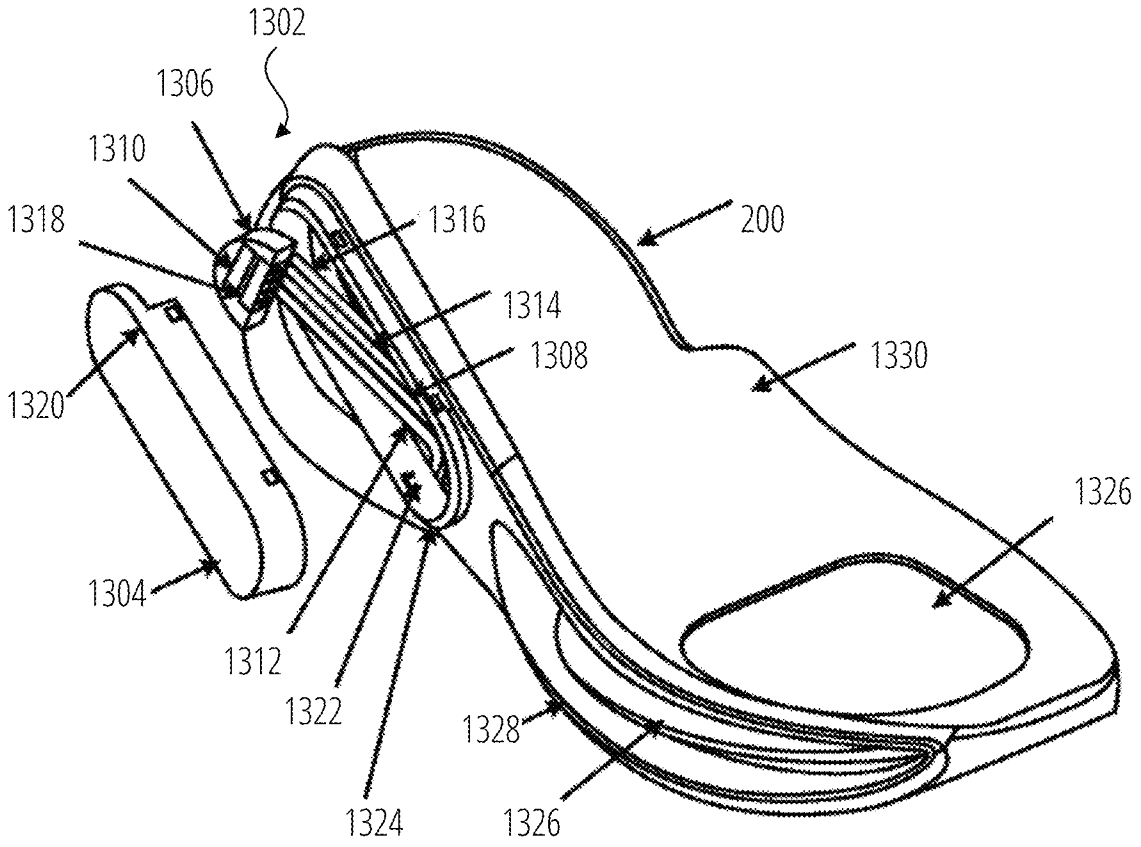
FIG. 13 is an exploded view of a sensory cushioning system having a fluid distributor connection, in an example embodiment.

FIG. 13 is an exploded view of sensory cushioning system 200 having a fluid distributor connection 1302, in an example embodiment. The fluid distributor connection 1302 may be specifically adapted to seat and enclose the motorized pump 216 of FIG. 12, but the fluid distributor connection 1302 may couple any suitable motorized pump 216.

The fluid distributor connection 1302 includes a housing 1304 to enclose the motorized pump 216, a connector 1306 configured to fluidly couple the manifold 1206 (FIG. 12) to the sole structure, fluid lines 1308, 1312, 1314, 1316 are coupled to the connector 1306, and a filter 1310 coupled to the connector 1306. A sealing system 1318 engages the connector 1306 to the manifold 1206. A housing recess 1320 engages with a frame recess 1322 to secure the housing 1304 to the frame 1324.

The sensory cushioning system 200 thereby includes multiple airbags 1326 which are fluidly coupled to the motorized pump 216. The motorized pump 216 allows for each airbag 1326 to be independently pressurized to a desired pressure, as disclosed herein.

Figure 14:
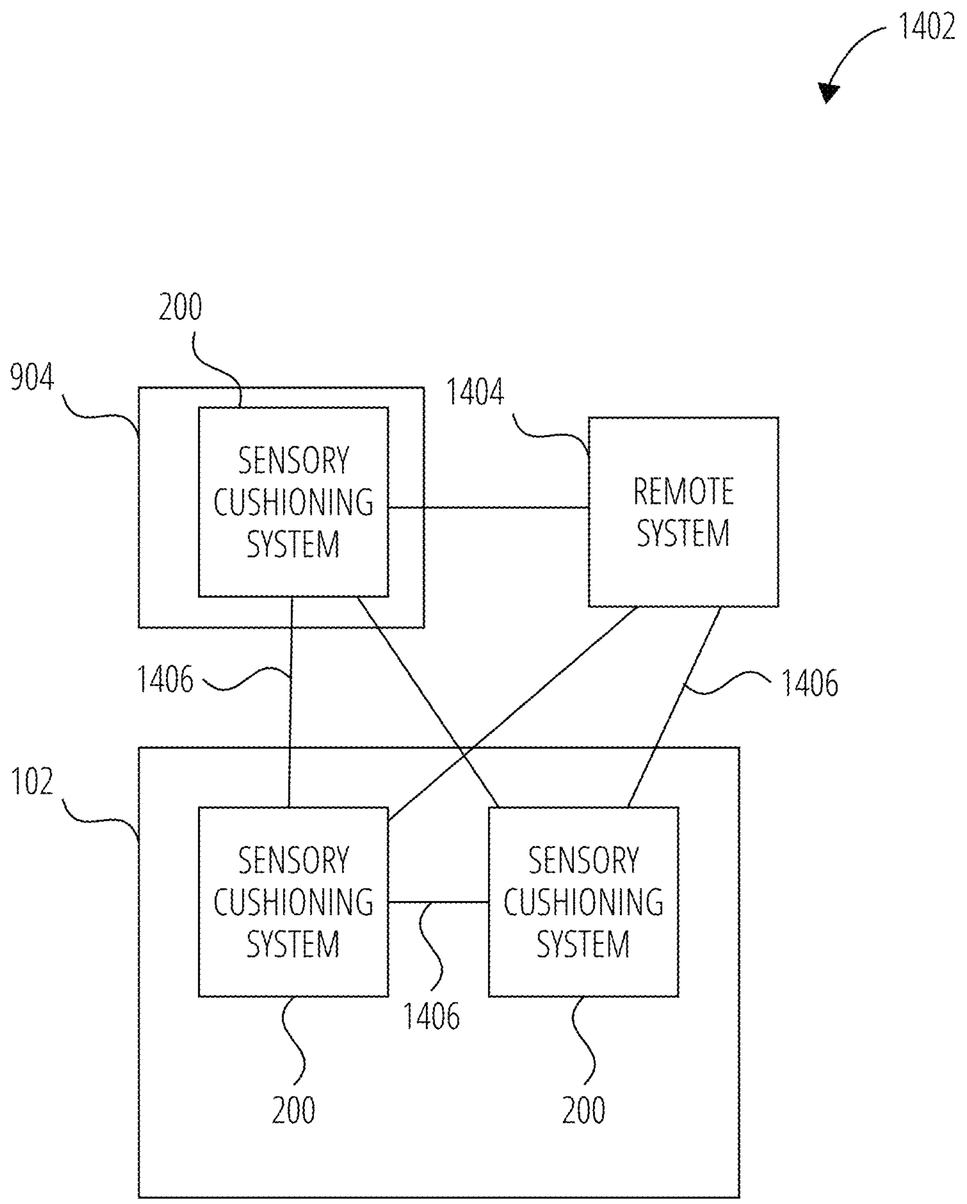
FIG. 14 is a block diagram of a Smart Electro-Adaptive Reactive Airbag System of devices which have sensory cushioning systems operating in conjunction with one another and with a remote system, in an example embodiment.

FIG. 14 is a block diagram of a SEARAS system 1402 of devices 102, 904 which have sensory cushioning systems 200 operating in conjunction with one another and with a remote system 1404, in an example embodiment. The SEARAS system 1402 may enhance, augment, and assist mobility, orientation, perception, and performance of a wearer. The SEARAS system 1402 may be a collection of devices 102, 904 configured to be worn by a particular wearer and which may be selected and configured to work in conjunction with one another to provide mobility-enhancement for that wearer though communication between and among the sensory cushioning systems 200 incorporated in the devices 102, 802, 904 and, optionally, a remote system 1404, such as a custom electronic device, smartphone, tablet computer, personal computer, or a remote, networked system, including cloud systems and other suitable systems which may be configured to provide enhanced computing or diagnostic power that is not necessarily present in any of the sensory cushioning systems 200 or wearable devices 102, 904 individually. Thus, the SEARAS system 1402 as illustrated may be utilized for a wearer who has had a leg amputated, in which the prosthetic limb 904 may provide a prosthetic limb while the enhanced wearable mobility article 102 may provide general body stability and safety while the wearer adapts to and utilizes the prosthetic limb 904. However, it is to be recognized and understood that the SEARAS system 1402 is provided for illustration and not limitation and that the principles disclosed with respect to the SEARAS system 1402 may be applied to any number of mobility-enhancing wearable articles across any number of wearers, locations, and environments.

In the illustrated example, the prosthetic limb 904 includes one sensory cushioning system 200 while the enhanced wearable mobility article 102 has multiple sensory cushioning systems 200. While two sensory cushioning systems 200 are illustrated with respect to the enhanced wearable mobility article 102, it is to be recognized and understood that any suitable number of sensory cushioning systems 200 may be implemented and included in a single enhanced wearable mobility article 102 or other suitable wearable device, e.g., the enhanced wearable mobility article 1002. Moreover, while the devices 102, 904 are illustrated, it is further to be recognized and understood that the SEARAS system 1402 may include any desired number of wearable devices that incorporate a sensory cushioning system 200.

Each individual sensory cushioning system 200 may utilize its communication module 210 (FIG. 2) to include or provide for one or more communication links 1406 that allow for the transmission of data between the sensory cushioning system 200 and any desired number of other sensory cushioning systems 200 in the SEARAS system 1402, both within a single wearable device, e.g., the enhanced wearable mobility article 102, or between wearable devices, e.g., between the enhanced wearable mobility article 102 and the prosthetic limb 904. Moreover, as illustrated, the sensory cushioning systems 200 include communication links 1406 with the remote system 1404, thereby allowing the remote system 1404 to receive information from the sensory cushioning system 200, in various examples, send information to each sensory cushioning system 200.

Consequently, on the basis of sensor data, e.g., data from the pressure sensors 204 and/or orientation sensors 214 of the various sensory cushioning systems 200 of the SEARAS system 1402, the individual wearable devices 102, 904 of the SEARAS system 1402 may adapt their operation accordingly. Thus, for instance, if the sensory cushioning system 200 of the prosthetic limb 904 detects a foot lift or footfall by the wearer, the enhanced wearable mobility article 102 may adapt its operation to provide general stability for the wearer, e.g., by stabilizing the legs or torso of the wearer through the exoskeleton function of the enhanced wearable mobility article 102. Or, conversely, if the sensory cushioning systems 200 of the enhanced wearable mobility article 102 detect that the wearer is pitching forward at an unusual rate, the sensory cushioning system 200 of the prosthetic limb 904 may motorized pump 216 of to increase or decrease the pressure in the sensory cushioning system 200 of the prosthetic limb 904 to soften or adapt the shock to the leg of the wearer or otherwise mitigate the effects of an anticipated hard or jarring impact. Consequently, while the SEARAS system 1402 may be comprised of individual devices 102, 904 which are configured to and capable of operating independently of one another, the SEARAS system 1402 may work to combine the operation of the devices 102, 904 into a unified and functional whole.

In addition to providing communications and processing and/or computing power for the SEARAS system 1402 generally, the remote system 1404 may further provide a user interface for control and diagnostic functions, among any other suitable functionality in service of the operation of the SEARAS system 1402. Thus, in an example, the remote system 1404 may provide a user interface to allow a user to set parameters for the operation of the individual devices 102, 904 of the SEARAS system 1402. Thus, the remote system 1404 may set parameters for how aggressive or moderate the response of the exoskeleton of the enhanced wearable mobility article 102 is, the reactivity of the changes in pressor provided by the motorized pump 216 of a sensory cushioning system 200, and so forth. The remote system 1404 may also present information related to the detection of the sensors of the sensory cushioning systems 200 and other telemetry and/or diagnostic information that may be of interest to a user of the remote system 1404, such as the wearer, a caregiver of the wearer, a coach or teammate of the wearer, and so forth. Such principles are disclosed in U.S. Pat. No. 10,327,672, SYSTEM AND METHO FOR ANALYZING ATHLETIC ACTIVITY, Giedwoyn, issued Jun. 25, 2019, which is incorporated by reference herein in its entirety.

Consequently, the SEARAS system 1402 may aid a wearer in adapting to various types of wearable devices having different cushioning systems and types, e.g., different articles of footwear having different levels of cushioning support, and/or advising the wearer regarding switching between and among the different cushioning systems, e.g., a sole with an airbag, a highly-developed midsole, a modestly developed midsole, etc. Additionally or alternatively, the SEARAS system 1402 may allow a sensory cushioning system 200 to simulate different kinds of cushioning systems to provide the wearer with different types of cushioning systems. Further additionally or alternatively, the SEARAS system 1402 may advise a wearer to switch between the SEARAS system 1402 and conventional wearable articles in order to reduce wear on the SEARAS system 1402.

Figure 15:
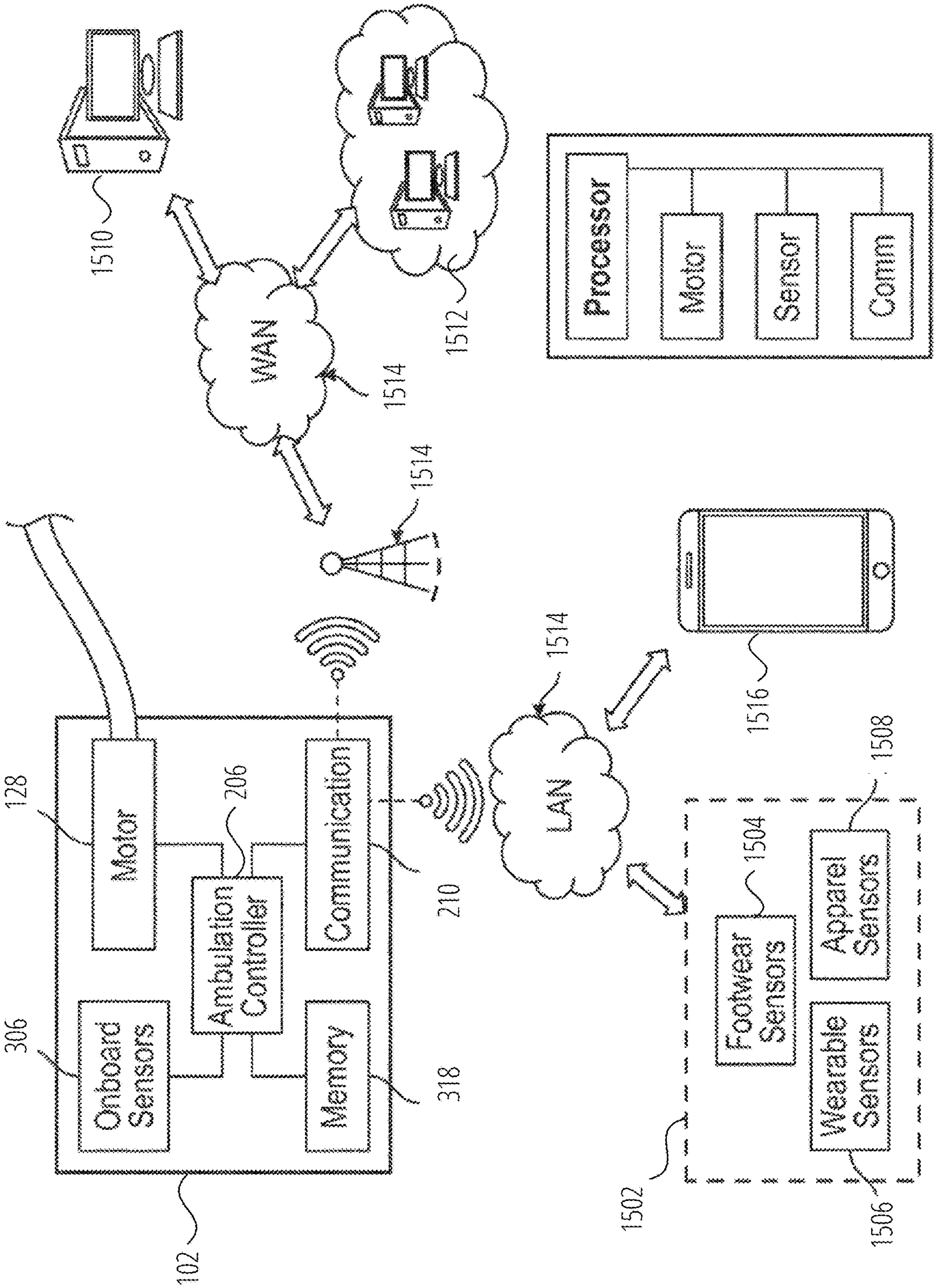
FIG. 15 is a schematic illustration of a Smart Electro-Adaptive Reactive Airbag System, in an example embodiment.

FIG. 15 is a schematic illustration of the SEARAS system 1402, in an example embodiment. The enhanced wearable mobility article 102 may be or otherwise include an integrated electronics package having control circuitry 304, the motor 128, the activity sensors 306, the computer readable memory device 318, and the communication circuit 320.

The communication circuit 320 may be in wireless communication with one or more remote sensors 1502 disposed on the user's body. As will be discussed below, these remote sensors 1502 may be configured to sense/monitor one or more biomechanical or biometric parameters of the wearer 104, and may provide this data to the control circuitry 206 for the purpose of understanding the motion or pose or activity level of the wearer 104. As generally illustrated, the remote sensors 1502 may include, for example, one or more accelerometers, inertial measurement units, gyroscopes, strain gauges, or force/pressure sensors connected to or embedded in a wearable article of the wearer, including an article of footwear, clothing, and/or on user-mounted wearable electronic devices (i.e., generally referred to as "footwear sensors 1504", "wearable sensors 1506", and "apparel sensors 1508"). Additionally, the communication module 210 may be in bidirectional communication with a remote host system 1510 or a remote host system 1510 via a wireless communication network 1514 (e.g., a wide area network (WAN) that includes any suitable infrastructure or computing devices that may be required to communicate over longer distances.

The remote host system 1510 may be implemented as a high-speed server computing device or a mainframe computer capable of handling bulk data processing and/or for storing user data, user parameters, and/or user configurations for use with or by the enhanced wearable mobility article 102. In some embodiments, the remote host system 1510 may operate as the host in a client-server interface for conducting any necessary data exchanges and communications with one or more "third party" servers to complete one or more transactions or data exchanges. The cloud computing system 1512, on the other hand, may operate as middleware for IoT (Internet of Things), WoT (Web of Things), Internet of Adaptive Apparel and Footwear (IoAAF), and/or M2M (machine-to-machine) services, connecting an assortment of heterogeneous electronic devices with a service-oriented architecture (SOA) via a data network. As an example, cloud computing system 1512 may be implemented as a middleware node to provide different functions for dynamically onboarding heterogeneous devices, multiplexing data from each of these devices, and routing the data through reconfigurable processing logic for processing and transmission to one or more destination applications. The wireless communication network 1514 may be any available type of network, including a combination of public distributed computing networks (e.g., Internet) and secured private networks (e.g., local area network, wide area network, virtual private network). It may also include wireless and wireline transmission systems (e.g., satellite, cellular network, terrestrial networks, etc.). In at least some aspects, most if not all data transaction functions carried out by the enhanced wearable mobility article 102 may be conducted over a wireless network, such as a wireless local area network (WLAN) or cellular data network, to ensure freedom of movement of the wearer 104.

The control circuitry 206 and associated sensors 306, 1504, 1506, 1508 may attempt to model and/or understand the dynamics and/or kinematics of the wearer 104 to discern when the wearer 104 is walking or running, and when the foot of the wearer 104 is about to enter a push off phase of a gait. The control circuitry 206 may include any one or various combinations of: a logic circuit, a dedicated control module, an electronic control unit, a processor, an application specific integrated circuit, or any suitable integrated circuit device, whether resident, remote or a combination of both. By way of example, the control circuitry 206 may include a plurality of microprocessors including a main processor and a secondary or parallel processor. The control circuitry 206, as used herein, may comprise any combination of hardware, software, and/or firmware disposed inside and/or outside of the structure of the enhanced wearable mobility article 102 (e.g., within a computer readable memory device 318), and may be configured to communicate with and/or control the transfer of data between the enhanced wearable mobility article 102 and a bus, computer, processor, device, service, and/or network. The control circuitry 206 is generally operable to execute any or all of the various computer program products, software, applications, algorithms, methods and/or other processes disclosed herein. Routines may be executed in real-time, continuously, systematically, sporadically and/or at regular intervals, for example, each 100 microseconds, 3.125, 6.25, 12.5, 25 and 100 milliseconds, etc., during ongoing use or operation of the control circuitry 206.

The control circuitry 206 may include or may communicate with a resident or remote memory device, such as a computer readable memory device 318 that is packaged inside the control circuitry 206. Resident memory may comprise semiconductor memory, including volatile memory (e.g., a random-access memory (RAM) or multiple RAM) and non-volatile memory (e.g., read only memory (ROM) or an EEPROM), magnetic-disk storage media, optical storage media, flash memory, etc. A resident power supply, such as a lithium ion battery with plug-in or cable-free (induction or resonance) rechargeable capabilities, may be embedded within the ambulation engine 23.

The communication module 210 may provide both long-range communication capabilities (e.g., for communication over the wireless communication network 1514) and/or close-range communication capabilities for communication with the more locally present remote sensors 1502 and/or a mobile device 1516. Long-range communication capabilities with remote networked devices may be provided via one or more or all of a cellular network chipset/component, a satellite service chipset/component, or a wireless modem or chipset/component. Close-range wireless connectivity may be provided via a BLUETOOTH® transceiver, a radio-frequency identification (RFID) tag, an NFC device, a DSRC component, and/or a radio antenna. Wireless communications may be further facilitated through implementation of a BLUETOOTH Low Energy (BLE), category (CAT) M1 or CAT-NB1 wireless interface.

The various enhanced wearable mobility articles disclosed herein, the SEARAS system 1402, and the sensory cushioning system 200 more generally, may be adapted for interaction with a virtual platform, such as a virtual reality, augmented reality, or within a video game context. In such cases, the various articles and systems disclosed herein may function as part of an Internet of Assistive and Adaptive Apparel and Footwear ("IoAAAF"). Such an IoAAAF may incorporate some or all of the elements of the Internet of Adaptive Apparel and Footwear ("IoAAF") system disclosed in Patent Cooperation Treaty Application PCT/US23/31679, ELECTROMECHANICAL AMBLITORY ASSIST DEVICE, Andon, which is incorporated by reference in its entirety. In such an example, the various enhanced wearable mobility articles may provide a user interface for the IoAÁAF or IoAAF, including receiving inputs from the wearer providing feedback to the wearer by way of the sensors of the sensory cushioning system 200. Further examples of IoAAFs which may be incorporated into the IoAÁAF disclosed herein are disclosed in U.S. Pat. No. 11,051,574, INTELLIGENT ELECTRONIC FOOTWEAR AND CONTROL LOGIC FOR AUTOMATED PEDESTRIAN COLLISION AVOIDANCE, Andon, issued Jul. 6, 2021; U.S. Pat. No. 10,681,954, INTELLIGENT ELECTRONIC FOOTWEAR AND CONTROL LOGIC FOR AUTOMATED INFRASTRUCTURE-BASED PEDESTRIAN TRACKING, Andon, issued Jun. 16, 2020; and U.S. Pat. No. 11,122,852, INTELLIGENT ELECTRONIC FOOTWEAR AND LOGIC FOR NAVIGATION ASSISTANCE BY AUTOMATED TACTILE, AUDIO, AND VISUAL FEEDBACK, Andon, issued Sep. 21, 2021, all of which are incorporated by reference herein in their entirety.

The SEARAS system 1402 and more generally the IoAÁAF may further be utilized in the context of determining the fit or utility of other components or elements of the IoAÁAF or IoAAF, as appropriate. For instance, the sensory cushioning system 200 may be utilized to determine the attributes or fit suitability of articles as disclosed in U.S. Pat. No. 18,827,366, WEARABLE ARTICLE SYSTEM WITH STRETCH SENSORS, Andon, and may be used in conjunction with U.S. Pat. No. 10,062,097, THREE-DIMENSIONAL BODY SCANNING AND APPAREL RECOMMENDATION, Andon, issued Aug. 28, 2018, both of which are incorporated by reference herein in their entirety. Such adaptation may be utilized in addition to the ability of the SEARAS system 1402 to adapt the components of the SEARAS system 1402, e.g., the sensory cushioning systems 200, to the fit or function of the wearer at any given time.

While this description details multiple specific embodiments of uses of the sensory cushioning system 200, it is to be recognized and understood that the sensory cushioning system 200 may be incorporated into any wearable article for which the functionality of the sensory cushioning system 200 may be advantageous. Thus, in an example, the sensory cushioning system 200 may be incorporated into a ski boot to detect when the wearer is engaged in vigorous skiing, in which case high pressure in the airbag 402 (FIG. 4A) is desired, or when the wearer is donning or doffing the ski boot, in which case low pressure in the airbag 402 may be desired. Such principles may be applied to any wearable article that is generally or desirably rigid but which, as a result, may be difficult don or doff, such as a hockey skate, knee brace, and the like. Such principles may also apply to a shin guard, as disclosed in U.S. Pat. No. 10,994,188, SHIN GUARD WITH REMOTE HAPTIC FEEDBACK, Andon, issued May 23, 2018, and which is incorporated by reference herein in its entirety.

Moreover, the principles described herein may further be applied to circumstances not directly related to overt or macro movement by the wearer. Thus, for instance, the sensory cushioning systems 200 may, in various examples, be positioned to detect respiration or other physiologic parameters of the wearer, e.g., pulse or other cardiac or respiratory factors. On the basis of such physiologic parameters as respiration rate, pulse, or other factors related to stress, anxiety, or mindfulness factors, the sensory cushioning system 200 and or the associate device, such as the enhanced wearable mobility article 102, may take steps to alert the wearer as to the physiologic state or take affirmative steps to calm or relax the wearer. For instance, the airbag 402 may have its pressure increased or decreased, and various airbags 402 across an enhanced wearable mobility article 102 or SEARAS system 1402 may be pressurized or depressurized in sequence to induce a soothing or massaging effect on the wearer, the haptic devices 212 may be pulsed to induce relaxing or soothing sensations, and so forth.

Example 1 is a sensory cushioning system, comprising: an airbag forming an interior volume and a pocket, wherein the interior volume is substantially airtight; an internal electronic assembly positioned within the pocket; an external electronic assembly positioned exterior to the airbag; and an interconnect electrically coupling the internal electronic assembly to the external electronic assembly.

In Example 2, the subject matter of Example 1 includes, wherein the internal electronic assembly comprises a pressure sensor configured to detect pressure placed on the airbag by an external force.

In Example 3, the subject matter of Example 2 includes, wherein the external electronic assembly comprises a haptic device configured to deliver haptic stimulation detectable external to the sensory cushioning system.

In Example 4, the subject matter of Example 3 includes, a motorized pump configured to increase and decrease a pressure within the interior volume.

In Example 5, the subject matter of Example 4 includes, a power source configured to power the motorized pump.

In Example 6, the subject matter of Examples 4-5 includes, control circuitry configured to control the operation of the motorized pump based, at least in part, on an output from the pressure sensor.

In Example 7, the subject matter of Example 6 includes, an orientation sensor, wherein the control circuitry is further configured to control the operation of the motorized pump based, at least, on output from the orientation sensor.

Example 8 is an enhanced mobility wearable article, comprising: a rigid frame comprising two portions and forming a structure configured to be secured to a body part of a wearer; a joint secured between two portions of the rigid frame, configured to allow the two portions to move with respect to one another about the joint; a motor, operatively coupled to the rigid frame, configured to cause the two portions to move with respect to one another about the joint; and a sensory cushioning system, secured to the rigid frame and configured to interface with the body part of the wearer, comprising: an airbag forming an interior volume and a pocket, wherein the interior volume is substantially airtight; an internal electronic assembly positioned within the pocket and including a pressure sensor; an external electronic assembly positioned exterior to the airbag; and an interconnect electrically coupling the internal electronic assembly to the external electronic assembly; a controller, operatively coupled to the sensory cushioning system and to the motor, wherein the controller is configured to operate the motor based, at least in part, on an output of the pressure sensor.

In Example 9, the subject matter of Example 8 includes, wherein the external electronic assembly comprises a haptic device configured to deliver haptic stimulation detectable external to the sensory cushioning system.

In Example 10, the subject matter of Example 9 includes, wherein the sensory cushioning system is configured to provide proprioceptive outputs detectable by the wearer in conjunction with the operation of the motor.

In Example 11, the subject matter of Example 10 includes, wherein the external electronic assembly comprises a haptic device configured to provide the proprioceptive output detectable by the wearer.

In Example 12, the subject matter of Example 11 includes, wherein the sensory cushioning system further comprises a motorized pump configured to increase and decrease a pressure within the interior volume.

In Example 13, the subject matter of Example 12 includes, wherein the controller is configured to cause the motorized pump to increase and decrease pressure within the interior volume in conjunction with the operation of the motor.

In Example 14, the subject matter of Example 13 includes, wherein the sensory cushioning system further comprises an orientation sensor, wherein the control circuitry is further configured to control the operation of the motorized pump and the motor based, at least, on output from the orientation sensor.

Example 15 is an enhanced mobility wearable article, comprising: a rigid frame configured to be secured to a body part of a wearer; a sensory cushioning system, secured to the rigid frame and configured to interface with the body part of the wearer, comprising: an airbag forming an interior volume and a pocket, wherein the interior volume is substantially airtight; an internal electronic assembly positioned within the pocket and including a pressure sensor; an external electronic assembly positioned exterior to the airbag; an interconnect electrically coupling the internal electronic assembly to the external electronic assembly; a motorized pump configured to increase and decrease a pressure within the interior volume; and control circuitry, operatively coupled to the motorized pump, configured to operate the motorized pump based, at least in part, on an output from the pressure sensor.

In Example 16, the subject matter of Example 15 includes, wherein the control circuit is configured to increase the pressure in the interior volume based on a relatively low pressure detected by the pressure sensor and decrease the pressure in the interior volume based on a relatively high pressure detected by the pressure sensor.

In Example 17, the subject matter of Example 16 includes, wherein the external electronic assembly comprises a haptic device configured to provide the proprioceptive output detectable by the wearer.

In Example 18, the subject matter of Example 17 includes, wherein the control circuitry is further configured to operate the haptic device based, at least in part, on the pressure sensed by the pressure sensor.

In Example 19, the subject matter of Examples 15-18 includes, wherein the sensory cushioning system further comprises an orientation sensor operatively coupled to the control circuitry.

In Example 20, the subject matter of Example 19 includes, wherein the control circuitry is configured to operate the motorized pump further based on an output of the orientation circuitry.

In Example 21, the subject matter of Example 20 includes, wherein the control circuitry is configured to reduce pressure in the interior volume if the orientation circuity indicates a falling motion by the wearer.

Example 22 is an enhanced mobility wearable article, comprising: a rigid frame configured to be secured to a body part of a wearer; a sensory cushioning system, secured to the rigid frame and configured to interface with the body part of the wearer, comprising: an airbag forming an interior volume and a pocket, wherein the interior volume is substantially airtight; an internal electronic assembly positioned within the pocket; an external electronic assembly positioned exterior to the airbag; an interconnect electrically coupling the internal electronic assembly to the external electronic assembly; an orientation sensor coupled to at least one of the internal electronic assembly and the external electronic assembly; a motorized pump configured to increase and decrease a pressure within the interior volume; and control circuitry, operatively coupled to the motorized pump, configured to operate the motorized pump based, at least in part, on an output from the orientation sensor.

In Example 23, the subject matter of Example 22 includes, wherein the orientation sensor comprises at least one of: a gyroscope, a magnetometer, or an accelerometer.

In Example 24, the subject matter of Examples 22-23 includes, wherein the orientation sensor is configured to detect a change in orientation indicative of a falling motion.

In Example 25, the subject matter of Example 24 includes, wherein the control circuity is configured to cause the motorized pump to reduce pressure in the interior volume based on the indication of the falling motion.

In Example 26, the subject matter of Example 25 includes, wherein the internal electronic assembly further comprises a pressure sensor configured to detect pressure placed on the airbag by an external force and wherein the control circuity is further configured to operate the motorized pump based, at least in part, on an output of the pressure sensor.

In Example 27, the subject matter of Example 26 includes, wherein the external electronic assembly comprises a haptic device configured to provide a proprioceptive output detectable by the wearer.

In Example 28, the subject matter of Example 27 includes, wherein the control circuity is configured to operate the haptic device in conjunction with the operation of the motorized pump.

Example 29 is an enhanced mobility wearable article, comprising: a rigid frame comprising two portions and forming a structure configured to be secured to a body part of a wearer; a joint secured between two portions of the rigid frame, configured to allow the two portions to move with respect to one another about the joint; a motor, operatively coupled to the rigid frame, configured to cause the two portions to move with respect to one another about the joint; and a sensory cushioning system, secured to the rigid frame and configured to interface with the body part of the wearer, comprising: an airbag forming an interior volume and a pocket, wherein the interior volume is substantially airtight; an internal electronic assembly positioned within the pocket and including a pressure sensor; an external electronic assembly positioned exterior to the airbag; an orientation sensor coupled to at least one of the internal electronic assembly and the external electronic assembly; and an interconnect electrically coupling the internal electronic assembly to the external electronic assembly; a controller, operatively coupled to the sensory cushioning system and to the motor, wherein the controller is configured to operate the motor based, at least in part, on an activity associated with the wearer.

In Example 30, the subject matter of Example 29 includes, wherein the controller is coupled to a user interface configured to receive an input indicative of the activity.

In Example 31, the subject matter of Example 30 includes, wherein the sensory cushioning system further comprises a communication module configured to communicate with the user interface to receive the input indicative of the activity.

In Example 32, the subject matter of Examples 29-31 includes, wherein the controller is further configured to identify the activity based, at least in part, on an output from the orientation sensor.

In Example 33, the subject matter of Example 32 includes, wherein the controller is further configured to identify the activity based, at least in part, on an output from the pressure sensor.

In Example 34, the subject matter of Examples 32-33 includes, wherein the sensory cushioning system is a first sensory cushioning system and further comprising a second sensory cushioning system operatively coupled to the controller, wherein the controller is further configured to identify the activity based on output from both the first and second sensory cushioning systems.

In Example 35, the subject matter of Examples 32-34 includes, wherein each of the first and second sensory cushioning systems further comprise a motorized pump configured to increase and decrease a pressure within the interior volume and wherein the controller is further configured to operate the motorized pump of each of the first and second sensory cushioning systems.

Example 36 is an enhanced mobility wearable article, comprising: a rigid frame comprising two portions and forming a structure configured to be secured to a body part of a wearer; a joint secured between two portions of the rigid frame, configured to allow the two portions to move with respect to one another about the joint; a motor, operatively coupled to the rigid frame, configured to cause the two portions to move with respect to one another about the joint; and a sensory cushioning system, secured to the rigid frame and configured to interface with the body part of the wearer, comprising: an airbag forming an interior volume and a pocket, wherein the interior volume is substantially airtight; an internal electronic assembly positioned within the pocket and including a pressure sensor; an external electronic assembly positioned exterior to the airbag; an orientation sensor coupled to at least one of the internal electronic assembly and the external electronic assembly; and an interconnect electrically coupling the internal electronic assembly to the external electronic assembly; a controller, operatively coupled to the sensory cushioning system and to the motor, wherein the controller is configured to operate the motor based, at least in part, on an output from the orientation sensor.

In Example 37, the subject matter of Example 36 includes, wherein the controller is further configured to operate the motor based on an indication from the orientation sensor that the wearer is falling.

In Example 38, the subject matter of Example 37 includes, wherein the controller is further configured to operate the motor based on an output from the pressure sensor.

In Example 39, the subject matter of Example 38 includes, wherein the controller is further configured to operate the motor based on the output from the pressure sensor indicating an increase in pressure detected by the pressure sensor.

In Example 40, the subject matter of Example 39 includes, wherein the controller is further configured to cause the motor to brace the wearer from a fall.

In Example 41, the subject matter of Example 40 includes, wherein the sensory cushioning system further comprises a motorized pump configured to increase and decrease a pressure within the interior volume.

In Example 42, the subject matter of Example 41 includes, wherein the controller is further configured to cause the motorized pump to adjust pressure in the interior volume based on the indication from the orientation sensor the wearer is falling.

Example 43 is a smart electro-adaptive reactive airbag system, comprising: a plurality of enhanced wearable mobility articles, each comprising: a rigid frame configured to be secured to a body part of a wearer; a sensory cushioning system, secured to the rigid frame and configured to interface with the body part of the wearer, comprising: an airbag forming an interior volume and a pocket, wherein the interior volume is substantially airtight; an internal electronic assembly positioned within the pocket and including a pressure sensor; an external electronic assembly positioned exterior to the airbag; an interconnect electrically coupling the internal electronic assembly to the external electronic assembly; a communication module configured to provide electronic communication with an external source; wherein the sensory cushioning system of each of the plurality of enhanced wearable mobility articles is configured to transmit an output of the pressure sensor to each of the other of the other sensory cushioning systems via the electronic communication provided by the communication module.

In Example 44, the subject matter of Example 43 includes, a remote system further configured to receive the output from the pressure sensor from each of the communication modules.

In Example 45, the subject matter of Example 44 includes, wherein at least one of the sensory cushioning systems includes an orientation sensor and wherein the communication module is further configured to transmit an output of the orientation sensor.

In Example 46, the subject matter of Example 45 includes, wherein at least one of the sensory cushioning systems further comprises: a motorized pump configured to increase and decrease a pressure within the interior volume; and control circuity, operatively coupled to the motorized pump and configured to operate the motorized pump based, at least in part, on the output of the pressure sensor from the sensory cushioning systems and from the output of the orientation sensor.

In Example 47, the subject matter of Example 46 includes, wherein each of the sensory cushioning systems comprises control circuity, an orientation sensor, and a motorized pump, and wherein each control circuitry is configured to operate its respective motorized pump based, at least in part, on the output of the pressure sensor and the orientation sensor of each of the sensory cushioning systems.

In Example 48, the subject matter of Examples 45-47 includes, wherein at least one of the enhanced wearable mobility articles further comprises: a joint secured between two portions of the rigid frame, configured to allow the two portions to move with respect to one another about the joint; a motor, operatively coupled to the rigid frame, configured to cause the two portions to move with respect to one another about the joint; and a controller, operatively coupled to the sensory cushioning system and to the motor, wherein the controller is configured to operate the motor based, at least in part, on the output of each of the pressure sensors and the orientation sensor.

In Example 49, the subject matter of Example 48 includes, wherein the controller is further configured to cause the control circuitry of the sensory cushioning system having the motorized pump to operate the motorized pump in conjunction with the operation of the motor.

Example 50 is at least one machine-readable medium including instructions that, when executed by processing circuitry, cause the processing circuitry to perform operations to implement of any of Examples 1-49.

Example 51 is an apparatus comprising means to implement of any of Examples 1-49.

Example 52 is a system to implement of any of Examples 1-49.

Example 53 is a method to implement of any of Examples 1-49.

What is claimed is:

1. A smart electro-adaptive reactive airbag system, comprising:

a plurality of enhanced wearable mobility articles, each comprising:

a rigid frame configured to be secured to a body part of a wearer; and a sensory cushioning system, secured to the rigid frame and configured to interface with the body part of the wearer, comprising:

an airbag forming an interior volume and a pocket, wherein the interior volume is substantially airtight;

an internal electronic assembly positioned within the pocket and including a pressure sensor;

an external electronic assembly positioned exterior to the airbag;

an interconnect electrically coupling the internal electronic assembly to the external electronic assembly; and a communication module configured to provide electronic communication with an external source;

wherein the sensory cushioning system of each of the plurality of enhanced wearable mobility articles is configured to transmit an output of the pressure sensor to each of the other of the sensory cushioning systems via the electronic communication provided by the communication module.

2. The smart electro-adaptive reactive airbag system of claim 1, further comprising a remote system further configured to receive the output from the pressure sensor from each of the communication modules.

3. The smart electro-adaptive reactive airbag system of claim 2, wherein at least one of the sensory cushioning systems includes an orientation sensor and wherein the communication module is further configured to transmit an output of the orientation sensor.

4. The smart electro-adaptive reactive airbag system of claim 3, wherein at least one of the sensory cushioning systems further comprises:

a motorized pump configured to increase and decrease a pressure within the interior volume; and control circuity, operatively coupled to the motorized pump and configured to operate the motorized pump based, at least in part, on the output of the pressure sensor from the sensory cushioning systems and from the output of the orientation sensor.

5. The smart electro-adaptive reactive airbag system of claim 4, wherein each of the sensory cushioning systems comprises control circuitry, an orientation sensor, and a motorized pump, and wherein each control circuitry is configured to operate its respective motorized pump based, at least in part, on the output of the pressure sensor and the orientation sensor of each of the sensory cushioning systems.

6. The smart electro-adaptive reactive airbag system of claim 3, wherein at least one of the enhanced wearable mobility articles further comprises:

a joint secured between two portions of the rigid frame, configured to allow the two portions to move with respect to one another about the joint;

a motor, operatively coupled to the rigid frame, configured to cause the two portions to move with respect to one another about the joint; and control circuitry, operatively coupled to the sensory cushioning system and to the motor, wherein the control circuitry is configured to operate the motor based, at least in part, on the output of each of the pressure sensors and the orientation sensor.

7. The smart electro-adaptive reactive airbag system of claim 6, wherein the control circuitry is further configured to cause the control circuitry of the sensory cushioning system having a motorized pump to operate the motorized pump in conjunction with operation of the motor.

8. The smart electro-adaptive reactive airbag system of claim 6, wherein the control circuitry is further configured to operate the motor based on an indication from the orientation sensor that the wearer is falling.

9. The smart electro-adaptive reactive airbag system of claim 8, wherein the control circuitry is further configured to cause the motor to brace the wearer from a fall.

10. The smart electro-adaptive reactive airbag system of claim 6, wherein the control circuitry is further configured to operate the motor based on the output from the pressure sensor indicating an increase in pressure detected by the pressure sensor.

11. A method of making a smart electro-adaptive reactive airbag system, comprising:

making a plurality of enhanced wearable mobility articles, each comprising the steps of:

obtaining a rigid frame configured to be secured to a body part of a wearer; and securing a sensory cushioning system to the rigid frame, the sensory cushioning system configured to interface with the body part of the wearer, comprising:

an airbag forming an interior volume and a pocket, wherein the interior volume is substantially airtight;

an internal electronic assembly positioned within the pocket and including a pressure sensor;

an external electronic assembly positioned exterior to the airbag;

an interconnect electrically coupling the internal electronic assembly to the external electronic assembly; and a communication module configured to provide electronic communication with an external source;

wherein the sensory cushioning system of each of the plurality of enhanced wearable mobility articles is configured to transmit an output of the pressure sensor to each of the other of the sensory cushioning systems via the electronic communication provided by the communication module.

12. The method of claim 11, further comprising obtaining a remote system configured to receive the output from the pressure sensor from each of the communication modules.

13. The method of claim 12, wherein at least one of the sensory cushioning systems includes an orientation sensor and wherein the communication module is further configured to transmit an output of the orientation sensor.

14. The method of claim 13, wherein at least one of the sensory cushioning systems further comprises:

a motorized pump configured to increase and decrease a pressure within the interior volume; and control circuity, operatively coupled to the motorized pump and configured to operate the motorized pump based, at least in part, on the output of the pressure sensor from the sensory cushioning systems and from the output of the orientation sensor.

15. The method of claim 14, wherein each of the sensory cushioning systems comprises control circuitry, an orientation sensor, and a motorized pump, and wherein each control circuitry is configured to operate its respective motorized pump based, at least in part, on the output of the pressure sensor and the orientation sensor of each of the sensory cushioning systems.

16. The method of claim 13, wherein at least one of the enhanced wearable mobility articles further comprises:

a joint secured between two portions of the rigid frame, configured to allow the two portions to move with respect to one another about the joint;

a motor, operatively coupled to the rigid frame, configured to cause the two portions to move with respect to one another about the joint; and control circuitry, operatively coupled to the sensory cushioning system and to the motor, wherein the control circuitry is configured to operate the motor based, at least in part, on the output of each of the pressure sensors and the orientation sensor.

17. The method of claim 16, wherein the control circuitry is further configured to cause the control circuitry of the sensory cushioning system having a motorized pump to operate the motorized pump in conjunction with operation of the motor.

18. The method of claim 16, wherein the control circuitry is further configured to operate the motor based on an indication from the orientation sensor that the wearer is falling.

19. The method of claim 18, wherein the control circuitry is further configured to cause the motor to brace the wearer from a fall.

20. The method of claim 16, wherein the control circuitry is further configured to operate the motor based on the output from the pressure sensor indicating an increase in pressure detected by the pressure sensor.

* * * * *